US007323553B2

(12) United States Patent
Fahrner et al.

(10) Patent No.: US 7,323,553 B2
(45) Date of Patent: Jan. 29, 2008

(54) NON-AFFINITY PURIFICATION OF PROTEINS

(75) Inventors: Robert Fahrner, San Mateo, CA (US); Deborah Follman, West Lafayette, IN (US); Benedicte Lebreton, San Francisco, CA (US); Robert van Reis, Emerald Hills, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 10/423,299

(22) Filed: Apr. 25, 2003

(65) Prior Publication Data

US 2003/0229212 A1    Dec. 11, 2003

Related U.S. Application Data

(60) Provisional application No. 60/375,953, filed on Apr. 26, 2002.

(51) Int. Cl.
*A23J 1/00* (2006.01)
(52) U.S. Cl. .................................. 530/412
(58) Field of Classification Search ............ 435/6, 435/7.1, 69.1; 530/412, 387.1; 436/828, 436/161; 210/650
See application file for complete search history.

(56) References Cited

U.S. PATENT DOCUMENTS

| | | | | |
|---|---|---|---|---|
| 4,515,893 | A | 5/1985 | Kung et al. | 435/240 |
| 4,816,567 | A | 3/1989 | Cabilly et al. | 530/387 |
| 5,091,313 | A | 2/1992 | Chang et al. | 435/240.27 |
| 5,256,294 | A | 10/1993 | van Reis | |
| 5,256,694 | A | 10/1993 | Wuest et al. | 514/549 |
| 5,490,937 | A | 2/1996 | van Reis | 210/637 |
| 5,534,615 | A | 7/1996 | Baker et al. | 530/350 |
| 5,622,700 | A | 4/1997 | Jardieu et al. | 424/144.1 |
| 5,672,347 | A | 9/1997 | Aggarwal et al. | 424/139.1 |
| 5,677,171 | A | 10/1997 | Hudziak et al. | 435/240.27 |
| 5,693,762 | A | 12/1997 | Queen et al. | 530/387.3 |
| 5,714,338 | A | 2/1998 | Fei et al. | 435/7.24 |
| 5,721,108 | A | 2/1998 | Robinson et al. | 435/7.23 |
| 5,725,856 | A | 3/1998 | Hudziak et al. | 424/130.1 |
| 5,736,137 | A | 4/1998 | Anderson et al. | 424/133.1 |
| 6,054,051 | A | 4/2000 | van Reis | 210/641 |

FOREIGN PATENT DOCUMENTS

| | | |
|---|---|---|
| WO | WO 93/04173 | 3/1993 |
| WO | WO 95/19181 | 7/1995 |
| WO | WO 95/23865 | 9/1995 |
| WO | WO 96/30046 | 10/1996 |
| WO | WO 96/40210 | 12/1996 |
| WO | WO 97/26912 | 7/1997 |
| WO | WO 98/06248 | 2/1998 |
| WO | WO 98/23761 | 6/1998 |
| WO | WO 98/45331 | 10/1998 |
| WO | WO 98/51793 | 11/1998 |
| WO | WO 00/75348 | 12/2000 |
| WO | WO 01/40309 | 6/2001 |

OTHER PUBLICATIONS

Kathy Liszewski, Stragedies for Mab purification include cation exchange and tangential flow, Aug. 1997, Genetic Engineering News, pp. 16 and 35.*
Aruffo et al., "CD44 Is the Principle Cell Surface Receptor for Hyaluronate", Cell, 61, 1990, pp. 1303-1313.
Berg et al., "Bispecific Antibodies that Mediate Killing of Cells Infected with Human Immunodeficiency Virus of Any Strain", Proc. Natl. Acad. Sci. USA, 88, Jun. 1991, pp. 4723-4727.
Boschetti, E. et al, "Genetic Engineering News", 20 (13), 2000, pp. 34 & 51.
Brennan et al., "Preparation of Bispecific Antibodies by Chemical Recombination of Monoclonal Immunoglobulin $G_1$ Fragments", Science, 229, Jul. 1985, pp. 81-83.
Brodeur et al., "Mouse-Human Myeloma Partners for the Production of Heterohybridomas", Monoclonal Antibody Production Techniques and Applications, New York: Marcel Dekker, Inc., 1987, pp. 51-63.
Carter et al., "High Level *Escherichia coli* Expression and Production of a Bivalent Humanized Antibody Fragment", Bio/Technology, 10, Feb. 1992, pp. 163-167.
Carter et al., "Humanization of an Anti-p185$^{HER2}$ Antibody For Human Cancer Therapy", Proc. Natl. Acad. Sci. USA, 89, May 1992, pp. 4285-4289.
Ceriani et al., "Biological Activity of Two Humanized Antibodies against Two Different Breast Cancer Antigens and Comparison to Their Original Murine Forms", Cancer Research (Suppl), 55, Dec. 1995, pp. 5852s-5856s.
Chamow et al., "A Humanized, Bispecific Immunoadhesin-Antibody That Retargets CD3$^+$ Effectors to Kill HIV-1-Infected Cells", Journal of Immunology, 153, 1994, pp. 4268-4280.
Chothia et al, "Canonical Structures for the Hypervariable Regions of Immunoglobulins", J. Mol. Biol., 196, 1987, pp. 901-917.
Choy et al., "Percentage of Anti-CD4 Monoclonal Antibody-Coated Lymphocytes In The Rheumatoid Joint Is Associated With Clinical Improvement", Arthritis Rheumatism, 39, Jan. 1996, pp. 52-56.
Clackson et al., "Making Antibody Fragments Using Phage Display Libraries", Nature, 352, Aug. 1991, pp. 624-628.
Desroches et al, "Regulation and Functional Involvement of Distinct Determinants of Leucocyte Function-Associated Antigen 1 (LFA-1) in T-Cell Activation In Vitro", Scand. J. Immunol., 33, 1991, pp. 277-286.
Dhainaut et al., "CDP571, A Humanized Antibody to Human Tumor Necrosis Factor-α: Safety, Pharmacokinetics, Immune Response, and Influence of the Antibody on Cytokine Concentrations in Patients with Septic Shock", Critical Care Medicine, 23 (9), 1995, pp. 1461-1469.
Duchosal et al., "Immunization of hu-PBL-SCID Mice and the Rescue of Human Monoclonal Fab Fragments Through Combinatorial Libraries", Nature, 355, Jan. 1992, pp. 258-262.

(Continued)

Primary Examiner—Robert B. Mondesi
(74) Attorney, Agent, or Firm—Deirdre L. Conley; Ginger R. Dreger, Esq.; Heller Ehrman LLP

(57) ABSTRACT

The present invention relates to a method for protein purification that involves the combination of non-affinity chromatography with HPTFF.

25 Claims, 5 Drawing Sheets

OTHER PUBLICATIONS

Ellis et al., "Engineered Anti-CD38 Monoclonal Antibodies for Immunotherapy of Multiple Myeloma", The Journal of Immunology, 155, 1995, pp. 925-937.

Goding, "Production of Monoclonal Antibodies", Monoclonal Antibodies: Principles and Practice, Academic Press, 1986, pp. 59-103.

Graziano et al., "Construction and Characterization of a Humanized Anti -γ-lg Receptor Type I (FcγRI) Monoclonal Antibody", The Journal of Immunology, 155, 1995, pp. 4996-5002.

Gruber et al., "Efficient Tumor Cell Lysis Mediated by a BiSpecificSingle Chain Antibody Expressed in *Escherichia coli*", Journal of Immunology, 152, 1994, pp. 5368-5374.

Gueffroy Ph.d., Donald E., "Buffers: A Guide for the Preparation and Use of Buffers in Biological Systems", Calbiochem Corporation, 1975, pp. 3-21.

Hildreth et al., "A Human Lymphocyte-Associated Antigen Involved in Cell-Mediated Lympholysis", European Journal of Immunology, 13, 1983, pp. 202-208.

Hoogenboom et al., "By-Passing Immunisation: Human Antibodies from Synthetic Repertoires of Germline $V_H$ Gene Segments Rearranged in Vitro", J. Mol. Biol., 227, 1992, pp. 381-388.

Hoogenboom et al., "Construction and Expression of Antibody-Tumor Necrosis Factor Fusion Proteins", Molecular Immunology, 28 (9), 1991, pp. 1027-1037.

Hourmant et al., "Administration of an Anti-CD11a Monoclonal Antibody in Recipients of Kidney Transplantation", Transplantation, 58 (3), Aug. 1994, pp. 377-380.

Jacobovits et al., "Germ-Line Transmission and Expression of a Human-Derived Yeast Artificial Chromosome", Nature, 362, Mar. 1993, pp. 255-258.

Jacobovits et al., "Analysis of Homozygous Mutant Chimeric Mice: Deletion of the Immunoglobin Heavy-Chain Joining Region Blocks B-Cell Development and Antibody Production", Proc. Natl. Acad. Sci. USA, 90, Mar. 1993, pp. 2551-2555.

Jones et al., "Replacing the Complementarity-Determining Regions in a Human Antibody with Those From a Mouse", Nature, 321, May 1986, pp. 522-525.

Jurcic et al., "Radiolabeled Anti-CD33 Monoclonal Antibody M195 for Myeloid Leukemias", Cancer Research (Suppl.), 55, Dec. 1995, pp. 5908s-5910s.

Juweid et al., "Treatment of Non-Hodgkin's Lymphoma with Radiolabeled Murine, Chimeric, or Humanized LL2, and Anti-CD22 Monoclonal Antibody", Cancer Research (Suppl.), 55, :Dec. 1995, pp. 5899s-5907s.

Kabat et al., "Sequences of Proteins of Immunological Interest", U.S. Dept. of Health and Human Services, National Institute of Health, 5th edition, 1, 1991, pp. 103-108 and 324-331.

Kim et al., "The Vascular Endothelial Growth Factor Proteins: Identification of Biologically Relevant Regions by Neutralizing Monoclonal Antibodies", Growth Factors, 7, 1992, pp. 53-64.

Kohler et al., "Continuous Cultures of Fused Cells Secreting Antibody of Predefined Specificity", Nature, 256, Aug. 1975, pp. 495-497.

Kostelny et al., "Formation of a Bispecific Antibody by the Use of Leucine Zippers", Journal of Immunology, 148, (5), Mar. 1992, pp. 1547-1553.

Kozbor et al., "A Human Hybrid Myeloma for Production of Human Monoclonal Antibodies", The Journal of Immunology, 133, (6), Dec. 1984, pp. 3001-3005.

Lindmark et al., "Binding of Immunoglobulins to Protein A and Immunoglobulin Levels in Mammalian Sera", Journal of Immunological Methods, 62, 1983, pp. 1-13.

Litton et al., "Antibody-Targeted Superantigen Therapy Induces Tumor-Infiltrating Lymphocytes, Excessive Cytokine Production, and Apoptosis in Human Colon Carcinoma", European Journal of Immunology, 26, 1996, pp. 1-9.

Lorenz et al., "In Vivo Blockade of TNF-α by Intravenous Infusion of a Chimeric Monoclonal TNF-α Antibody in Patients with Rheumatoid Arthritis", The Journal of Immunology, 156, 1996, pp. 1646-1653.

Marks et al., "By-Passing Immunization: Building High Affinity Human Antibodies by Chain Shuffling", Bio/Technology, 10, Jul. 1992, pp. 779-783.

Marks et al., "By-Passing Immunization: Human Antibodies from V-gene Libraries Displayed on Phage", Journal of Molecular Biology, 222, 1991, pp. 581-597.

McCafferty et al., "Phage Antibodies: Filamentous Phage Displaying Antibody Variable Domains", Nature, 348, Dec. 1990, pp. 552-554.

Milstein et al., "Hybrid Hybridomas and Their Use in Immunohistochemistry", Nature, 305, Oct. 1983, pp. 537-540.

Morimoto et al., "Single-Step Purification of F(ab')$_2$ Fragments of Mouse Monoclonal Antibodies (Immunoglobulins Gl) by Hydrophobic Interaction High Performance Liquid Chromatography Using TSKgel Phenyl-5PW", Journal of Biochemical and Biolphysical Methods, 24, 1992, pp. 107-117.

Morrison et al., "Chimeric Human Antibody Molecules: Mouse Antigen-Binding Domains with Human Constant Region Domains", Proc. Natl. Acad. Sci. USA, 81, Nov. 1984, pp. 6851-6855.

Nakao, et al., "Separation of Proteins by Charged Ultrafiltration Membranes", Desalination 70, 1998, pp. 191-205.

Nishimura et al., "The Role of Lymphokine-Activated Cell-Associated Antigen-III. Inhibition of T-Cell Activation by Monoclonal Killer-Blocking Antibody", Cellular Immunology, 107, 1987, pp. 32-39.

Nishimura et al., "Lymphokine-Activated Cell Associated Antigen Involved in Broad-Reactive Killer Cell-Mediated Cytotoxicity", Cellular Immunology, 94, 1985, pp. 122-132.

Olive et al., "Human Lymphocyte Functional Antigens", pp. 173-185.

Presta et al., "Humanization of an Antibody Directed Against IgE", Journal of Immunology, 151, (5); Sep. 1993, pp. 2623-2632.

Richman et al., "Radioimmunotherapy for Breast Cancer Using Escalating Fractionated Doses of I-Labeled Chimeric L6 Antibody with Peripheral Blood Progenitor Cell Transfusions", Cancer Research (Suppl.); 55; Dec. 1995, pp. 5916s-5920s.

Riechmann, et al, "Reshaping Human Antibodies for Therapy", Nature, 332, Mar. 1988, pp. 323-327.

Saksena et al., "Effect of Solution pH and Ionic Strength on the Separation of Albumin from Immunoglobulins (IgG) by Selective Filtration", Biotechnology and Bioengineering, 43, 1994, pp. 960-968.

Santambien et al., "Bioprocess Tutorial: Rapid 'On Chip' Protein Analysis & Purification/Process Proteomics Integrates Protein Production Using Ciphergen's Protein Chip Technology", Genetic Engineering News, 22, (13), Jul. 2002, pp. 1-5.

Semba et al., "A *v-erbB*-related Protoncogene, c-erbB-2, is Distinct from the C-erbB-1/Epidermal Growth Factor-Receptor Gene and is Amplified in a Human Salivary Gland Adenocarcinoma", Proc. Natl. Acad. Sci. USA, 82, Oct. 1985, pp. 6497-6501.

Shalaby et al., "Development of Humanized Bispecific Antibodies Reactive with Cytotoxic Lymphocytes and Tumor Cells Overexpressing the HER2 Protooncogene", Journal of Experimental Medicine, 175, Jan. 1992, pp. 217-225.

Sharkey et al., "Evaluation of a Complementarity-Determining Region-Grafted (Humanized) Anti-Carcinoembryonic Antigen Monoclonal Antibody in Preclinical and Clinical Studies", Cancer Research (Suppl.), 55, Dec. 1995, pp. 5935s-5945s.

Sims et al., "A Humanized CD18 Antibody Can Block Function Without Cell Destruction", The Journal of Immunology, 151, (4), Aug. 1993, pp. 2296-2308.

Springer et al., "LFA-1 and Lyt-2,3, Molecules Associated with T Lymphocyte-Mediated Killing and Mac-1, and LFA-1 Homologue Associated with Complement Receptor Function," Immunological Rev., 68, 1982, pp. 171-195.

St. John et al., "Immunologic Therapy for ARDS, Septic Shock, and Multiple-Organ Failure", Chest 103, 1993, pp. 932-943.

Stamenkovic et al., "The B Lymphocyte Adhesion Molecule CD22 Interacts with Leukocyte Common Antigen CD45RO on T Cells and α2-6 Sialyltransferase, CD75, on B Cells", Cell, 66, 1991, pp. 1133-1144.

Stoppa et al., "Anti-LFA1 Monoclonal Antibody (25.3) for Treatment of Steroid-Resistant Grade III-IV Acute Graft-Versus-Host Disease", Transplant Intl., 4, 1991, pp. 3-7.

Traunecker, et al., "Bispecific Single Chain Molecules (Janusins) Target Cytotoxic Lymphocytes on HIV Infected Cells", The EMBO Journal, 10, (12), 1991, pp. 3655-3659.

Tutt et al., "Trispecific F(ab')3 Derivatives That Use Cooperative Signaling Via the TCR/CDR Complex and CD2 to Activate and Redirect Resting Cytotoxic T Cells", Journal of Immunology, 147, (1), 1991, pp. 60-69.

van Reis et al., "Protein Ultrafiltration", Encyclopedia of Bioprocess Technology: Fermentation, Biocatalysis, and Bioseparation, M.C. Flickinger and S.W. Drew, John Wiley & Sons, Inc., 1999, pp. 2197-2214.

van Reis et al., "High Performance Tangential Flow Filtration", Biotechnology and Bioengineering, 56, (1); Oct. 1997, pp. 71-82.

van Reis et al., "High Performance Tangential Flow Filtration Using Charged Membranes", Journal of Membrane Science, 159, 1999, pp. 133-142.

Vaughan et al., "Human Antibodies with Sub-Nanomolar Affinities Isolated from a Large Non-Immunized Phage Display Library", Nature Biotechnology, 14, Mar. 1996, pp. 309-314.

Verhoeyen et al., "Reshaping Human Antibodies: Grafting an Antilysozyme Activity", Science, 239, Mar. 1998, pp. 1534-1536.

Waterhouse et al., "Combinatorial Infection and In Vivo Recombination: A Strategy for Making Large Phage Antibody Repertoires", Nucleic Acids Research, 21, (9), 1993, pp. 2265-2266.

Yamamoto et al., "Similarity of Protein Encoded by the Human C-erb-B-2 Gene to Epidermal Growth Factor Receptor", Nature, 319 (16), Jan. 1986, pp. 230-234.

Zapata et al., "Engineering Linear F(ab')2 Fragments for Efficient Production in *Escherichia coli* and Enhanced Antiproliferative Activity", Protein Engineering, 8, (10), 1995, pp. 1057-1062.

Zeman et al., "Basic Chemistry and Physics of MF/UF Membranes and Their Precursors", Microfiltration and Ultrafiltration: Principles and Applications, New York, NY: Marcel Dekker, Inc., 1996, pp. 3-11.

Zeman et al., "Salute and Solvent Transport", Microfiltration and Ultrafiltration: Principles and Applications, New York, NY: Marcel Dekker, Inc., 1996, pp. 299-301.

Zydney et al., "High-Performance Tangential-Flow Filtration", Membrane Separations in Biotechnology, 2nd. ed., New York, N.Y.: Marcel Dekker, Inc., 10, 2001, pp. 277-301.

Christy et al., "High-Performance Tangential Flow Filtration: A High Highly Selective Membrane Separation Process", Elsevier, 144:133-136 (2002).

* cited by examiner

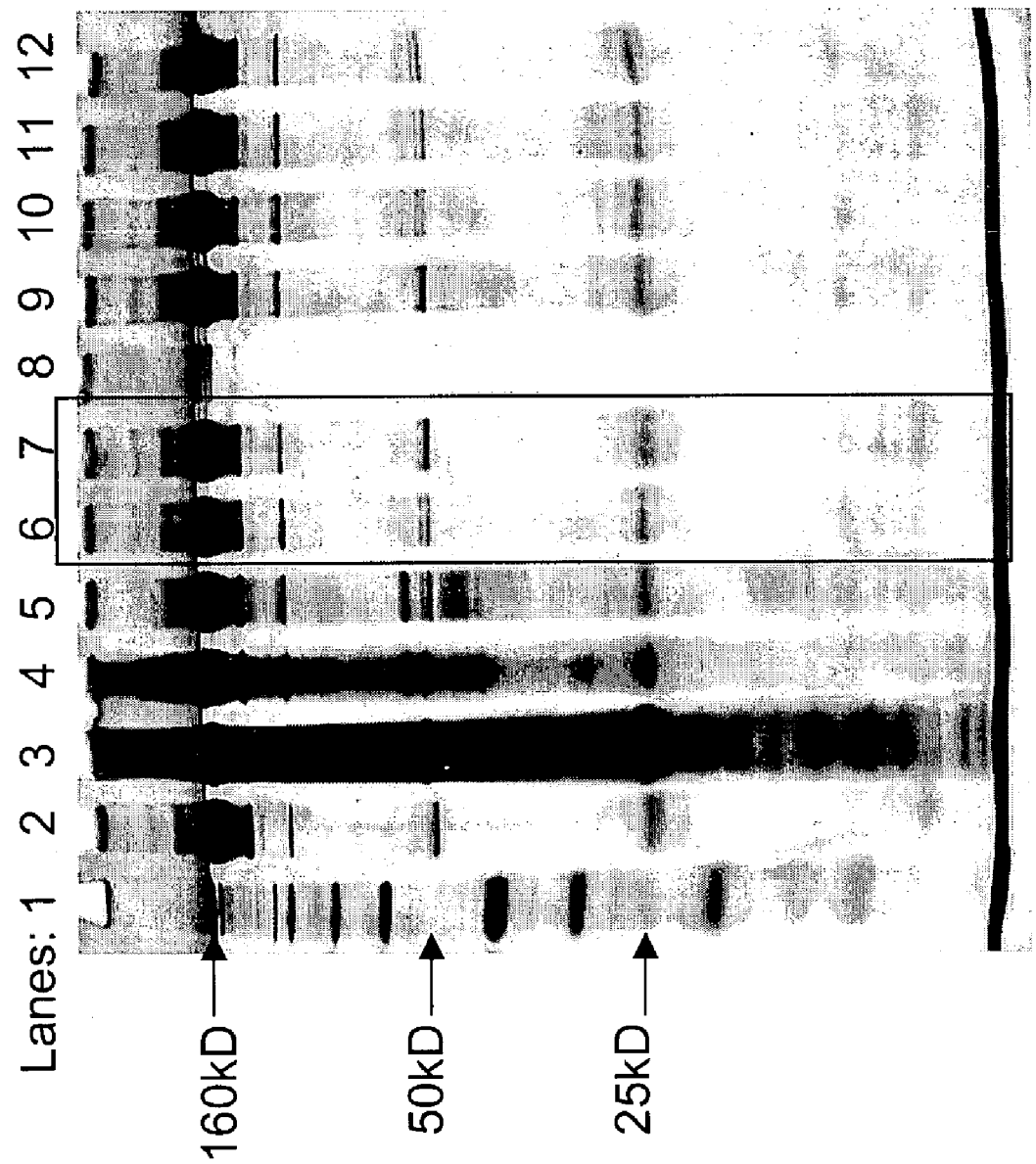

FIGURE 3

Full length anti-HER2 rhuMAb light chain and heavy chain amino acid sequences:

Figure 3A    anti-HER2 rhuMAb Light chain:

Asp Ile Gln Met Thr Gln Ser Pro Ser Ser Leu Ser Ala Ser Val Gly Asp Arg Val Thr Ile Thr Cys Arg Ala Ser Gln Asp Val Asn Thr Ala Val Ala Trp Tyr Gln Gln Lys Pro Gly Lys Ala Pro Lys Leu Leu Ile Tyr Ser Ala Ser Phe Leu Tyr Ser Gly Val Pro Ser Arg Phe Ser Gly Ser Arg Ser Gly Thr Asp Phe Thr Leu Thr Ile Ser Ser Leu Gln Pro Glu Asp Phe Ala Thr Tyr Tyr Cys Gln Gln His Tyr Thr Thr Pro Pro Thr Phe Gly Gln Gly Thr Lys Val Glu Ile Lys Arg Thr Val Ala Ala Pro Ser Val Phe Ile Phe Pro Pro Ser Asp Glu Gln Leu Lys Ser Gly Thr Ala Ser Val Val Cys Leu Leu Asn Asn Phe Tyr Pro Arg Glu Ala Lys Val Gln Trp Lys Val Asp Asn Ala Leu Gln Ser Gly Asn Ser Gln Glu Ser Val Thr Glu Gln Asp Ser Lys Asp Ser Thr Tyr Ser Leu Ser Ser Thr Leu Thr Leu Ser Lys Ala Asp Tyr Glu Lys His Lys Val Tyr Ala Cys Glu Val Thr His Gln Gly Leu Ser Ser Pro Val Thr Lys Ser Phe Asn Arg Gly Glu Cys (SEQ ID NO:1)

Figure 3B    anti-HER2 rhuMAb Heavy chain:

Glu Val Gln Leu Val Glu Ser Gly Gly Gly Leu Val Gln Pro Gly Gly Ser Leu Arg Leu Ser Cys Ala Ala Ser Gly Phe Asn Ile Lys Asp Thr Tyr Ile His Trp Val Arg Gln Ala Pro Gly Lys Gly Leu Glu Trp Val Ala Arg Ile Tyr Pro Thr Asn Gly Tyr Thr Arg Tyr Ala Asp Ser Val Lys Gly Arg Phe Thr Ile Ser Ala Asp Thr Ser Lys Asn Thr Ala Tyr Leu Gln Met Asn Ser Leu Arg Ala Glu Asp Thr Ala Val Tyr Tyr Cys Ser Arg Trp Gly Gly Asp Gly Phe Tyr Ala Met Asp Tyr Trp Gly Gln Gly Thr Leu Val Thr Val Ser Ser Ala Ser Thr Lys Gly Pro Ser Val Phe Pro Leu Ala Pro Ser Ser Lys Ser Thr Ser Gly Gly Thr Ala Ala Leu Gly Cys Leu Val Lys Asp Tyr Phe Pro Glu Pro Val Thr Val Ser Trp Asn Ser Gly Ala Leu Thr Ser Gly Val His Thr Phe Pro Ala Val Leu Gln Ser Ser Gly Leu Tyr Ser Leu Ser Ser Val Val Thr Val Pro Ser Ser Ser Leu Gly Thr Gln Thr Tyr Ile Cys Asn Val Asn His Lys Pro Ser Asn Thr Lys Val Asp Lys Lys Val Glu Pro Lys Ser Cys Asp Lys Thr His Thr Cys Pro Pro Cys Pro Ala Pro Glu Leu Leu Gly Gly Pro Ser Val Phe Leu Phe Pro Pro Lys Pro Lys Asp Thr Leu Met Ile Ser Arg Thr Pro Glu Val Thr Cys Val Val Val Asp Val Ser His Glu Asp Pro Glu Val Lys Phe Asn Trp Tyr Val Asp Gly Val Glu Val His Asn Ala Lys Thr Lys Pro Arg Glu Glu Gln Tyr Asn Ser Thr Tyr Arg Val Val Ser Val Leu Thr Val Leu His Gln Asp Trp Leu Asn Gly Lys Glu Tyr Lys Cys Lys Val Ser Asn Lys Ala Leu Pro Ala Pro Ile Glu Lys Thr Ile Ser Lys Ala Lys Gly Gln Pro Arg Glu Pro Gln Val Tyr Thr Leu Pro Pro Ser Arg Glu Glu Met Thr Lys Asn Gln Val Ser Leu Thr Cys Leu Val Lys Gly Phe Tyr Pro Ser Asp Ile Ala Val Glu Trp Glu Ser Asn Gly Gln Pro Glu Asn Asn Tyr Lys Thr Thr Pro Pro Val Leu Asp Ser Asp Gly Ser Phe Phe Leu Tyr Ser Lys Leu Thr Val Asp Lys Ser Arg Trp Gln Gln Gly Asn Val Phe Ser Cys Ser Val Met His Glu Ala Leu His Asn His Tyr Thr Gln Lys Ser Leu Ser Leu Ser Pro Gly (SEQ ID NO: 2)

FIGURE 4

Anti-CD11a mature antibody protein amino acid sequence:

Figure 4A     anti-CD11a rhuMAb Light chain:

DIQMTQSPSSLSASVGDRVTITCRASKTISKYLAWYQQKPGKAPKLLIYSGSTLQSGVPSRFS
GSGSGTDFTLTISSLQPEDFATYYCQQHNEYPLTFGQGTKVEIKRTVAAPSVFIFPPSDEQLKS
GTASVVCLLNNFYPREAKVQWKVDNALQSGNSQESVTEQDSKDSTYSLSSTLTLSKADYEK
HKVYACEVTHQGLSSPVTKSFNRGEC (SEQ ID NO:3)

Figure 4B     anti-CD11a rhuMAb Heavy chain:

EVQLVESGGGLVQPGGSLRLSCAASGYSFTGHWMNWVRQAPGKGLEWVGMIHPSDSETRY
NQKFKDRFTISVDKSKNTLYLQMNSLRAEDTAVYYCARGIYFYGTTYFDYWGQGTLVTVSS
ASTKGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPREEQYNSTYRVVSV
LTVLHQDWLNGKEYKCKVSNKALPAPIEKTISKAKGQPREPQVYTLPPSREEMTKNQVSLTCL
VKGFYPSDIAVEWESNGQPENNYKTTPPVLDSDGSFFLYSKLTVDKSRWQQGNVFSCSVMHE
ALHNHYTQKSLSLSPGK (SEQ ID NO:4)

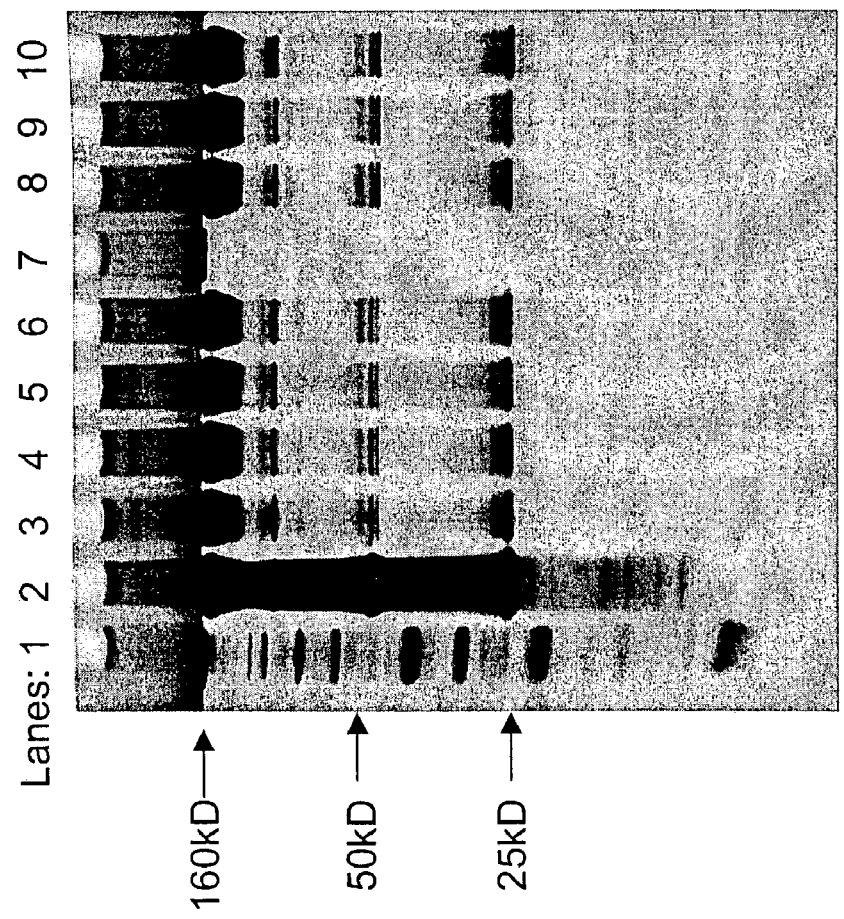

NON-AFFINITY PURIFICATION OF PROTEINS

CROSS-REFERENCE TO RELATED APPLICATIONS

This is a non-provisional application filed under 37CFR 1.53(b), claiming priority under USC Section 119(e) to provisional Application Ser. No. 60/375,953 filed Apr. 26, 2002.

BACKGROUND OF THE INVENTION

1. Field of the Invention

This invention relates generally to protein purification. In particular, the invention relates to a method for purifying proteins (such as antibodies and antibody-like molecules, e.g. immunoadhesins) from a composition comprising the polypeptide and at least one impurity without the use of affinity chromatography.

2. Description of the Related Art

The large-scale, economic purification of proteins is increasingly an important problem for the biotechnology industry. Generally, proteins are produced by cell culture, using either mammalian or bacterial cell lines engineered to produce the protein of interest by insertion of a recombinant plasmid containing the gene for that protein. Since the cell lines used are living organisms, they must be fed with a complex growth medium, containing sugars, amino acids, and growth factors, usually supplied from preparations of animal serum. Separation of the desired protein from the mixture of compounds fed to the cells and from the by-products of the cells themselves to a purity sufficient for use as a human therapeutic poses a formidable challenge.

Procedures for purification of proteins from cell debris initially depend on the site of expression of the protein. Some proteins are caused to be secreted directly from the cell into the surrounding growth media; others are made intracellularly. For the latter proteins, the first step of a purification process involves lysis of the cell, which can be done by a variety of methods, including mechanical shear, osmotic shock, or enzymatic treatments. Such disruption releases the entire contents of the cell into the homogenate, and in addition produces subcellular fragments that are difficult to remove due to their small size. These are generally removed by centrifugation or by filtration. The same problem arises, although on a smaller scale, with directly secreted proteins due to the natural death of cells and release of intracellular host cell proteins in the course of the protein production run.

Once a solution containing the protein of interest is obtained, its separation from the other proteins produced by the cell is usually attempted using a combination of different chromatography techniques. These techniques separate mixtures of proteins on the basis of their charge, degree of hydrophobicity, or size. Several different chromatography resins are available for each of these techniques, allowing accurate tailoring of the purification scheme to the particular protein involved. The essence of each of these separation methods is that proteins can be caused either to move at different rates down a long column, achieving a physical separation that increases as they pass further down the column, or to adhere selectively to the separation medium, being then differentially eluted by different solvents. In some cases, the desired protein is separated from impurities when the impurities specifically adhere to the column, and the protein of interest does not, that is, the protein of interest is present in the "flow-through."

Ion-exchange chromatography, named for the exchangeable counterion, is a procedure applicable to purification of ionizable molecules. Ionized molecules are separated on the basis of the non-specific electrostatic interaction of their charged groups with oppositely charged molecules attached to the solid phase support matrix, thereby retarding those ionized molecules that interact more strongly with solid phase. The net charge of each type of ionized molecule, and its affinity for the matrix, varies according to the number of charged groups, the charge of each group, and the nature of the molecules competing for interaction with the charged solid phase matrix. These differences result in resolution of various molecule types by ion-exchange chromatography. In typical protein purification using ion exchange chromatography, a mixture of many proteins derived from a host cell, such as in mammalian cell culture, is applied to an ion-exchange column. After non-binding molecules are washed away, conditions are adjusted, such as by changing pH, counter ion concentration and the like in step- or gradient-mode, to release from the solid phase a non-specifically retained or retarded ionized protein of interest and separating it from proteins having different charge characteristics. Anion exchange chromatography involves competition of an anionic molecule of interest with the negative counter ion for interaction with a positively charged molecule attached to the solid phase matrix at the pH and under the conditions of a particular separation process. By contrast, cation exchange chromatography involves competition of a cationic molecule of interest with the positive counter ion for a negatively charged molecule attached to the solid phase matrix at the pH and under the conditions of a particular separation process. Mixed mode ion exchange chromatography involves the use of a combination of cation and anion exchange chromatographic media in the same step. In particular, "mixed-mode" refers to a solid phase support matrix to which is covalently attached a mixture of cation exchange, anion exchange, and hydrophobic interaction moieties. A commercially available representative of mixed-mode ion exchange chromatographic columns is ABx™, the use of which is described in the Examples.

Hydroxyapatite chromatography of proteins involves the non-specific interaction of the charged amino or carboxylate groups of a protein with oppositely charged groups on the hydroxyapatite, where the net charge of the hydroxyapatite and protein are controlled by the pH of the buffer. Elution is accomplished by displacing the non-specific protein-hydroxyapatite pairing with ions such as $Ca^{2+}$ or $Mg^{2+}$. Negatively charged protein groups are displaced by negatively charged compounds, such as phosphates, thereby eluting a net-negatively charged protein.

Hydrophobic interaction chromatography (HIC) is useful for the purification and separation of molecules, such as proteins, based on differences in their surface hydrophobicity. Hydrophobic groups of a protein interact non-specifically with hydrophobic groups coupled to the chromatography matrix. Differences in the number and nature of protein surface hydrophobic groups results in differential retardation of proteins on an HIC column and, as a result, separation of proteins in a mixture of proteins.

Hydrophobic charge induction (HCI) chromatography is useful for the separation of biological molecules, such as proteins, based on the pH-dependent behavior of ionizable, dual-mode ligands (Boschetti, E. et al., Genetic Engineering News 20(13) (2000)). At neutral pH, the ligand is uncharged and binds a protein of interest via mild non-specific hydrophobic interaction. As pH is reduced during a buffer gradient, the ligand becomes positively charged and hydrophobic binding is disrupted by electrostatic charge repulsion (Boschetti, E. (2000), supra). The gentle conditions used in HCI reduces the risk of protein denaturation and antibody aggregation.

Affinity chromatography, which exploits a specific structurally dependent (i.e., spatially complementary) interaction between the protein to be purified and an immobilized capture agent, is a standard purification option for some proteins, such as antibodies. Protein A, for example, is a useful adsorbent for affinity chromatography of proteins, such as antibodies, which contain an Fc region. Protein A is a 41kD cell wall protein from *Staphylococcus aureas* which binds with a high affinity (about $10^{-8}$M to human IgG) to the Fc region of antibodies. Despite its common use, affinity chromatography is costly, particularly at the industrial scale necessary to purify therapeutic proteins.

High-performance tangential-flow filtration (HPTFF) is a membrane technology useful for the separation of protein mixtures without limit to their relative size (Zydney, A. L. and van Reis, R., High-Performance Tangential-Flow Filtration, ch. 10, in *Membrane Separations in Biotechnology*, 2d ed., William K. Wang, ed., Marcel Dekker, Inc., NY, N.Y. (2001), pp. 277-298; van Reis, R. et al. Biotechnol. Bioeng. 56:71-82 (1997); and van Reis, R., U.S. Pat. No. 5,256,694, U.S. Pat. No. 5,490,937, and U.S. Pat. No. 6,054,051, the contents of which are hereby incorporated by reference in their entirety). HPTFF can be used throughout the downstream purification process to remove specific impurities (such as proteins, DNA, or endotoxins), clear viruses, and/or eliminate protein oligomers or degradation products. HPTFF is unique among available separation technologies in that it can effect simultaneous purification, concentration, and buffer exchange, allowing several different separations steps to be combined into a single scalable unit operation.

Despite these advanced chromatography and filtration methods, affinity chromatography is often employed as a capture step to meet the purity, yield, and throughput requirements for pharmaceutical antibody purification. The high cost and instability of affinity media, however, increases the ultimate cost of antibody therapeutics, particularly those requiring high doses and/or chronic administration. In addition, adequate purity often is not achieved unless several purification steps are combined, thereby further increasing cost and reducing product yield. Antibodies account for an increasingly large percentage of therapeutic products on the market and in development in the United States for the treatment of, for example, cancer, autoimmune disease, infectious disease, cardiovascular disease, and transplant rejection (Stratan, F. et al., Monoclonal Antibodies—Coming of Age, 1 (2001), and Booth, M. et al., Monoclonal Antibodies: Targeting the Issues, 1 (2001)). Consequently, there is a need for processes that purify protein therapeutics or other polypeptide compounds using fewer steps and without the need for a costly affinity step.

SUMMARY OF THE INVENTION

The present invention relates to the surprising finding that a non-affinity chromatographic purification process in combination with HPTFF is capable of purifying a target protein, such as an antibody or an antibody-like molecule, from a mixture containing host cell proteins such that host cell protein impurities are present in the final purified target protein in an amount less than 100 parts per million (ppm).

In one aspect, the invention concerns a method for purifying a target protein from a mixture containing a host cell protein and optionally further impurities, comprising two non-affinity purification steps followed by high-performance tangential-flow filtration (HPTFF), in the absence of an affinity chromatography step, wherein such method produces a purified target protein containing less than 100 parts per million (ppm) of the host cell protein, alternatively less than 90 ppm, less than 80 pmm, less than 70 ppm, less than 60 ppm, less than 50 ppm, less than 40 ppm, less than 30 ppm, less than 20 ppm, less than 10 ppm, less than 5 ppm, or less than 3 ppm.

In a particular embodiment, the first and second non-affinity chromatography purification steps are different and are selected from the group consisting of ion exchange chromatography and hydrophobic interaction chromatography. For example, the ion exchange chromatography step may be cation exchange chromatography, anion exchange chromatography and/or mixed mode ion exchange chromatography. In a preferred embodiment, the first and second non-affinity purification steps are cation exchange chromatography and anion exchange chromatography, in either order. In another preferred embodiment, the first non-affinity purification step is cation exchange chromatography and said second non-affinity purification step is anion exchange chromatography. In yet another preferred embodiment, the method of the invention comprises two non-affinity chromatography purification steps followed by HPTFF and followed by an isolation step, to the exclusion of any other purification steps.

The target protein to be purified can be any protein, in particular recombinant protein produced in any host cell, including but not limited to, Chinese hamster ovary (CHO) cells. Optional target proteins are antibodies, immunoadhesins and other antibody-like molecules, such as fusion proteins including a $C_H2/C_H3$ region.

In another aspect, the invention concerns a method for purifying a target protein from a mixture containing a host cell protein and optionally further impurities, comprising one non-affinity chromatography purification step followed by high-performance tangential-flow filtration (HPTFF), in the absence of an affinity chromatography step, wherein such method produces a purified target protein containing less than 100 parts per million (ppm) of the host cell protein, alternatively less than 90 ppm, less than 80 pmm, less than 70 ppm, less than 60 ppm, less than 50 ppm, less than 40 ppm, less than 30 ppm, less than 20 ppm, less than 10 ppm, less than 5 ppm, or less than 3 ppm These and other non-limiting embodiments of the present invention are readily understood by one of ordinary skill in the art upon reading the disclosure and claims provided herein. It is understood that this invention is not limited to the particular compositions of matter and processes described, as such compounds and methods may, of course, vary. It is also to be understood that the terminology used herein is for the purpose of describing particular embodiments only, and is not intended to be limiting.

BRIEF DESCRIPTION OF THE DRAWINGS

FIG. 2 shows a silver-stained (Zaxis 10-20%) polyacrylamide gel, containing samples that were taken at different intervals during the purification of anti-HER2 rhuMAb and were subjected to SDS-PAGE analysis. The arrows indicating 160 kD, 50 kD, and 25 kD point to the full length antibody, the heavy chain, and the light chain, respectively. Other bands are anti-HER2 rhuMAb fragments. Samples included a molecular weight standard (lane 1), reference rhuMAb obtained using an affinity-purification process (lanes 2 and 7), a sample of rhuMAb harvested cell culture fluid (HCCF) (lane 3) prior to purification, and samples of material recovered, after S chromatography (lane 4), after Q chromatography (lane 5), after additional HPTFF (lanes 6 and 12), after HPTFF Experiment 1 using CRC100+ (lane 9), after HPTFF Experiment 1 using CRC300+ (lane 10), and after HPTFF Experiment 2 (lane 11).

FIGS. 3A and 3B. FIG. 3A is the amino acid sequence of the anti-HER2 rhuMAb light chain; FIG. 3B is the amino acid sequence of the anti-HER2 rhuMAb heavy chain.

FIGS. 4A and 4B. FIG. 4A is the amino acid sequence of the anti-CD11a rhuMAb light chain; FIG. 4B is the amino acid sequence of the anti-CD11a rhuMAb heavy chain.

FIG. 5 shows a silver-stained SDS-PAGE gel containing samples that were taken at different points during the purification of anti-CD40 recombinant human monoclonal antibody (rhuMAb)

DETAILED DESCRIPTION OF EMBODIMENTS

A. Definitions

Figure 1:
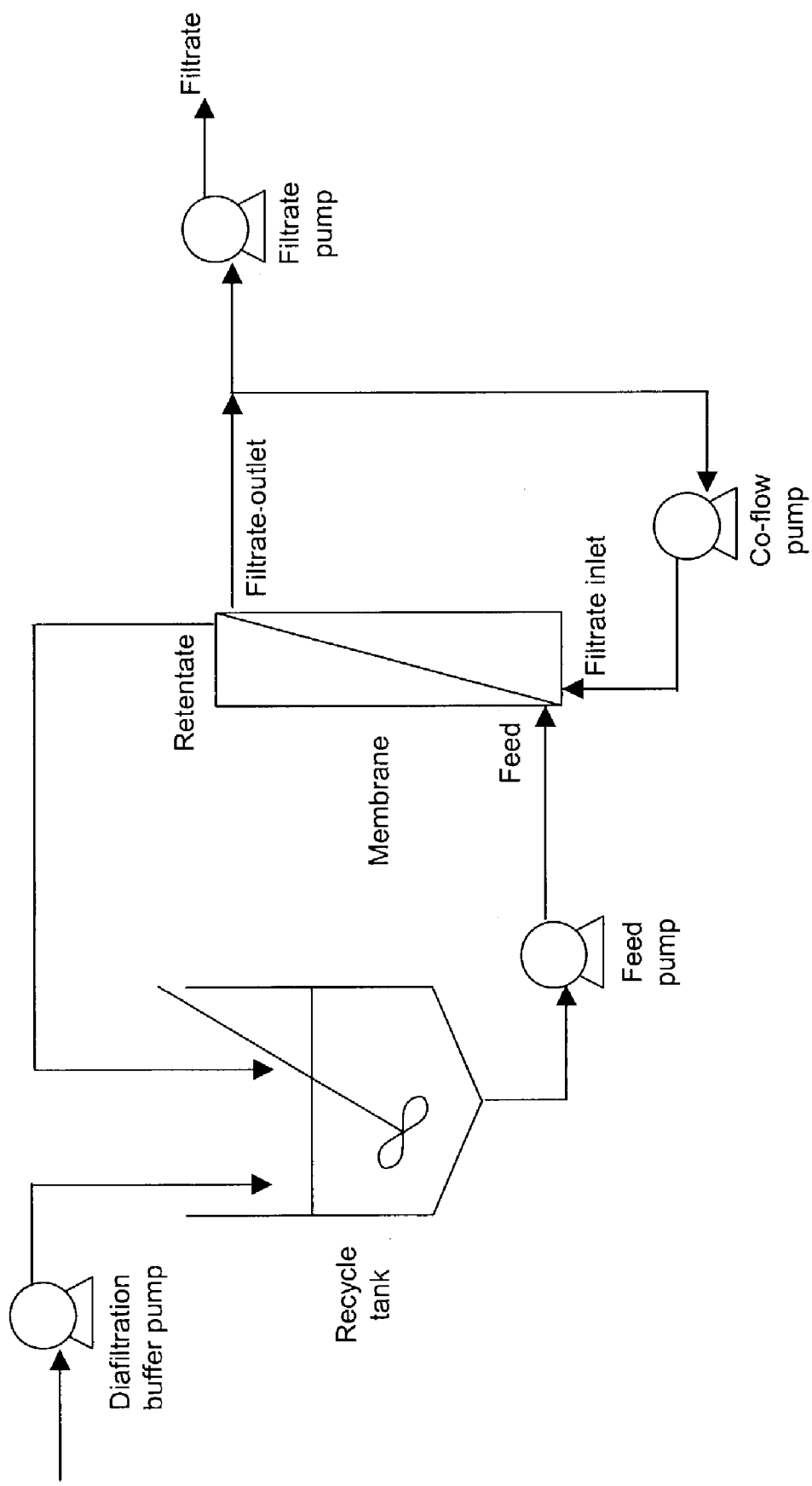
FIG. 1 shows a schematic diagram of the filtration set-up for HPTFF experiments.

The term "antibody" is used in the broadest sense and specifically covers monoclonal antibodies (including full length monoclonal antibodies), polyclonal antibodies, multispecific antibodies (e.g., bispecific antibodies), and antibody fragments so long as they retain, or are modified to comprise, a ligand-specific binding domain. The antibody herein is directed against an "antigen" of interest. Preferably, the antigen is a biologically important polypeptide and administration of the antibody to a mammal suffering from a disease or disorder can result in a therapeutic benefit in that mammal. However, antibodies directed against nonpolypeptide antigens (such as tumor-associated glycolipid antigens; see U.S. Pat. No. 5,091,178) are also contemplated. Where the antigen is a polypeptide, it may be a transmembrane molecule (e.g. receptor) or ligand such as a growth factor. Exemplary antigens include those polypeptides discussed above. Preferred molecular targets for antibodies encompassed by the present invention include CD polypeptides such as CD3, CD4, CD8, CD19, CD20, CD34, and CD40; members of the HER receptor family such as the EGF receptor, HER2, HER3 or HER4 receptor; cell adhesion molecules such as LFA-1, Mac1, p150,95, VLA-4, ICAM-1, VCAM and av/b3 integrin including either a or b subunits thereof (e.g. anti-CD11a, anti-CD18 or anti-CD11b antibodies); growth factors such as VEGF; IgE; blood group antigens; flk2/flt3 receptor; obesity (OB) receptor; mpl receptor; CTLA-4; polypeptide C etc. Soluble antigens or fragments thereof, optionally conjugated to other molecules, can be used as immunogens for generating antibodies. For transmembrane molecules, such as receptors, fragments of these (e.g. the extracellular domain of a receptor) can be used as the immunogen. Alternatively, cells expressing the transmembrane molecule can be used as the immunogen. Such cells can be derived from a natural source (e.g. cancer cell lines) or may be cells which have been transformed by recombinant techniques to express the transmembrane molecule.

"Antibody fragments" comprise a portion of a full length antibody, generally the antigen binding or variable region thereof. Examples of antibody fragments include Fab, Fab', F(ab')$_2$, and Fv fragments; single-chain antibody molecules; diabodies; linear antibodies; and multispecific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature* 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature* 352:624-628 (1991) and Marks et al., *J. Mol. Biol.* 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)).

The term "hypervariable region" when used herein refers to the amino acid residues of an antibody which are responsible for antigen-binding. The hypervariable region comprises amino acid residues from a "complementarity determining region" or "CDR" (i.e. residues 24-34 (L1), 50-56 (L2) and 89-97 (L3) in the light chain var domain and 31-35 (H1), 50-65 (H2) and 95-102 (H3) in the heavy chain variable domain; Kabat et al., *Sequences of Proteins of Immunological Interest,* 5th Ed. Public Health Service, National Institutes of Health, Bethesda, Md. (1991)) and/or those residues from a "hypervariable loop" (i.e. residues 26-32 (L1), 50-52 (L2) and 91-96 (L3) in the variable domain and 26-32 (H1), 53-55 (H2) and 96-101 (H3) in the heavy chain variable domain; Chothia and Lesk *J. Mol. Biol.* 196:901-917 (1987)). "Framework" or "FR" residues are those variable domain residues other than the hypervariable region residues as herein defined.

"Humanized" forms of non-human (e.g., murine) antibodies are chimeric antibodies which contain minimal sequence derived from non-human immunoglobulin. For the most part, humanized antibodies are human immunoglobulins (recipient antibody) in which hypervariable region residues of the recipient are replaced by hypervariable region residues from a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992).

As used herein, the term "immunoadhesin" designates antibody-like molecules which combine the "binding domain" of a heterologous "adhesin" protein (e.g. a receptor, ligand or enzyme) with the effector functions of an immunoglobulin constant domain. Structurally, the immunoadhesins comprise a fusion of the adhesin amino acid sequence with the desired binding specificity which is other than the antigen recognition and binding site (antigen combining site) of an antibody (i.e. is "heterologous") and an immunoglobulin constant domain sequence. The immunoglobulin constant domain sequence in the immunoadhesin is preferably derived from γ1, γ2, or γ4 heavy chains since immunoadhesins comprising these regions can be purified by Protein A chromatography (Lindmark et al., *J. Immunol. Meth.* 62:1-13 (1983)).

The term "ligand binding domain" as used herein refers to any native cell-surface receptor or any region or derivative thereof retaining at least a qualitative ligand binding of a corresponding native receptor. In a specific embodiment, the receptor is from a cell-surface polypeptide having an extracellular domain which is homologous to a member of the immunoglobulin super gene family. Other receptors, which are not members of the immunoglobulin super gene family but are nonetheless specifically covered by this definition, are receptors for cytokines, and in particular receptors with tyrosine kinase activity (receptor tyrosine kinases), members of the hematopoietin and nerve growth factor receptor superfamilies, and cell adhesion molecules, e.g. (E-, L- and P-) selecting.

The term "receptor binding domain" is used to designate any native ligand for a receptor, including cell adhesion molecules, or any region or derivative of such native ligand retaining at least a qualitative receptor binding ability of a corresponding native ligand. This definition, among others, specifically includes binding sequences from ligands for the above-mentioned receptors.

An "antibody-immunoadhesin chimera" comprises a molecule which combines at least one binding domain of an antibody (as herein defined) with at least one immunoadhesin (as defined in this application). Exemplary antibody-immunoadhesin chimeras are the bispecific CD4-IgG chimeras described in Berg et al., *PNAS (USA)* 88:4723-4727 (1991) and Chamow et al., *J. Immunol.* 153:4268 (1994).

Unless indicated otherwise, the term "HER2" when used herein refers to human HER2 protein and "HER2" refers to human HER2 gene. The human HER2 gene and HER2 protein are described in Semba et al., *PNAS (USA)* 82:6497-6501 (1985) and Yamamoto et al. *Nature* 319:230-234 (1986) (Genebank accession number X03363), for example.

"Trastuzumab," "HERCEPTIN®," "anti-HER2 rhuMAb," and "HER2" are used interchangeably herein to refer to a humanized anti-HER2 antibody comprising the light chain amino acid sequence of SEQ ID NO:1 and the heavy chain amino acid sequence of SEQ ID NO:2 or amino acid sequence variants thereof which retain the ability to bind HER2 and inhibit growth of tumor cells which overexpress HER2 (FIGS. 3A and 3B; see also U.S. Pat. No. 5,677,171, expressly incorporated herein by reference).

"Anti-CD11a rhuMAb" or "CD11a" are used interchangeably herein to refer to a humanized anti-CD11a antibody comprising the light chain amino acid sequence of SEQ ID NO:3 and the heavy chain amino acid sequence of SEQ ID NO:4 or amino acid sequence variants thereof which retain the ability to bind LFA-1 and to inhibit certain T-cell dependent immune functions (FIGS. 4A and 4B; see also U.S. Pat. No. 5,622,700; WO 98/23761; Steppe et al., *Transplant Intl.* 4:3-7 (1991); and Hourmant et al. *Transplantation* 58:377-380 (1994); which references are expressly incorporated herein by reference). Anti-CD11a antibodies further include, e.g., MHM24 [Hildreth et al., *Eur. J. Immunol.,* 13: 202-208 (1983)], R3.1 (IgG1) [R. Rothlein, Boehringer Ingelheim Pharmaceuticals, Inc., Ridgefield, Conn.], 25-3 (or 25.3), an IgG1 available from Immunotech, France [Olive et al., in Feldmann, ed., *Human T cell Clones. A new Approach to Immune Regulation,* Clifton, N.J., Humana, 1986 p. 173], KBA (IgG2a) [Nishimura et al., *Cell. Immunol.,* 107: 32 (1987); Nishimura et al., ibid., 94: 122 (1985)], M7/15 (IgG2b) [Springer et al., *Immunol. Rev.,* 68: 171 (1982)], IOT16 [Vermot Desroches et al., *Scand. J. Immunol.,* 33: 277-286 (1991)], SPVL7 [Vermot Desroches et al., supra], and M17 (IgG2a), available from ATCC, which are rat anti-murine CD11a antibodies. Preferred anti-CD11a antibodies are the humanized antibodies described in U.S. Pat. No. 6,037,454. It is also generally preferred that the anti-CD11a antibodies are not T-cell depleting antibodies, that is, that the administration of the anti-CD11a antibody does not reduce the level of circulating T-cells."

The "composition" to be purified herein comprises the polypeptide of interest and one or more impurities. The composition may be "partially purified" (i.e. having been subjected to one or more purification steps, such as by non-affinity chromatography described herein or may be obtained directly from a host cell or organism producing the polypeptide (e.g. the composition may comprise harvested cell culture fluid).

As used herein, "polypeptide" refers generally to peptides and proteins having more than about ten amino acids. Preferably, the polypeptide is a mammalian protein, examples of which include renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor -alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; Protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins (IGFBPs); CD proteins such as CD3, CD4, CD8, CD19 CD20, CD34, and CD40; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA-4 and VCAM; a tumor associated antigen such as HER2, HER3 or HER4 receptor; and fragments and/or variants of any of the above-listed polypeptides. In addition, a protein or polypeptide of the invention is an antibody, fragment or variant thereof, that binds specifically to any of the above-listed polypeptides.

An "impurity" is a material that is different from the desired polypeptide product or protein of interest. The impurity includes, but is not limited to, a host cell protein (HCP, such as CHOP), a polypeptide other than the target polypeptide, nucleic acid, endotoxin etc.

An "acidic variant" is a variant of a polypeptide of interest which is more acidic (e.g. as determined by cation exchange chromatography) than the polypeptide of interest. An example of an acidic variant is a deamidated variant.

The term "protein of interest" and "target protein" are used interchangeably and refer to a protein or polypeptide such as an antibody (as defined herein) that is to be purified by a method of the invention from a mixture of proteins and, optionally, other materials such as cell debris and the like.

The terms "Chinese hamster ovary cell protein" and "CHOP" are used interchangeably to refer to a mixture of host cell proteins ("HCP") derived from a Chinese hamster ovary ("CHO") cell culture. The HCP or CHOP is generally present as an impurity in a cell culture medium or lysate (e.g., a harvested cell culture fluid ("HCCF")) comprising a protein of interest such as an antibody or immunoadhesin expressed in a CHO cell.) The amount of CHOP present in a mixture comprising a protein of interest provides a measure of the degree of purity for the protein of interest. HCP or CHOP includes, but is not limited to, a protein of interest expressed by the host cell, such as a CHO host cell. Typically, the amount of CHOP in a protein mixture is expressed in parts per million relative to the amount of the protein of interest in the mixture. It is understood that where the host cell is another mammalian cell type, an *E. coli*, a yeast, an insect cell, or a plant cell, HCP refers to the proteins, other than target protein, found in a lysate of the host cell.

The term "parts per million" or "ppm" are used interchangeably herein to refer to a measure of purity of the protein of interest purified by a method of the invention. The units ppm refer to the amount of HCP or CHOP in nanograms/milliliter per protein of interest in milligrams/milliliter (i.e., CHOP ppm=(CHOP ng/ml)/(protein of interest mg/ml), where the proteins are in solution). Where the proteins are dried (such as by lyophilization), ppm refers to (CHOP ng)/(protein of interest mg)).

By "purifying" a polypeptide from a composition comprising the polypeptide and one or more impurities is meant increasing the degree of purity of the polypeptide in the composition by removing (completely or partially) at least one impurity from the composition. According to the present invention, purification is performed without the use of an affinity chromatography step. A "purification step" may be part of an overall purification process resulting in a "homogeneous" composition, which is used herein to refer to a composition comprising less than 100 ppm HCP in a composition comprising the protein of interest, alternatively less than 90 ppm, less than 80 ppm, less than 70 ppm, less than 60 ppm, less than 50 ppm, less than 40 ppm, less than 30 ppm, less than 20 ppm, less than 10 ppm, less than 5 ppm, or less than 3 ppm.

The terms "Protein A" and "ProA" are used interchangeably herein and encompasses Protein A recovered from a native source thereof, Protein A produced synthetically (e.g. by peptide synthesis or by recombinant techniques), and variants thereof which retain the ability to bind proteins which have a $C_H2/C_H3$ region, such as an Fc region. Protein A can be purchased commercially from Repligen, Pharmacia and Fermatech. Protein A is generally immobilized on a solid phase support material. The term "ProA" also refers to an affinity chromatography resin or column containing chromatographic solid support matrix to which is covalently attached Protein A.

The term "chromatography" refers to the process by which a solute of interest in a mixture is separated from other solutes in a mixture as a result of differences in rates at which the individual solutes of the mixture migrate through a stationary medium under the influence of a moving phase, or in bind and elute processes.

The term "affinity chromatography" and "protein affinity chromatography" are used interchangeably herein and refer to a protein separation technique in which a protein of interest or antibody of interest is reversibly and specifically bound to a biospecific ligand. Preferably, the biospecific ligand is covalently attached to a chromatographic solid phase material and is accessible to the protein of interest in solution as the solution contacts the chromatographic solid phase material. The protein of interest (e.g., antibody, enzyme, or receptor protein) retains its specific binding affinity for the biospecific ligand (antigen, substrate, cofactor, or hormone, for example) during the chromatographic steps, while other solutes and/or proteins in the mixture do not bind appreciably or specifically to the ligand. Binding of the protein of interest to the immobilized ligand allows contaminating proteins or protein impurities to be passed through the chromatographic medium while the protein of interest remains specifically bound to the immobilized ligand on the solid phase material. The specifically bound protein of interest is then removed in active form from the immobilized ligand with low pH, high pH, high salt, competing ligand, and the like, and passed through the chromatographic column with the elution buffer, free of the contaminating proteins or protein impurities that were earlier allowed to pass through the column. Any component can be used as a ligand for purifying its respective specific binding protein, e.g. antibody.

The terms "non-affinity chromatography" and "non-affinity purification" refer to a purification process in which affinity chromatography is not utilized. Non-affinity chromatography includes chromatographic techniques that rely on non-specific interactions between a molecule of interest (such as a protein, e.g. antibody) and a solid phase matrix.

The term "specific binding" as used herein, such as to describe interactions between a molecule of interest and a ligand bound to a solid phase matrix, refers to the generally reversible binding of a protein of interest to a ligand through the combined effects of spatial complementarity of protein and ligand structures at a binding site coupled with electrostatic forces, hydrogen bonding, hydrophobic forces, and/or van der Waals forces at the binding site. The greater the spatial complementarity and the stronger the other forces at the binding site, the greater will be the binding specificity of a protein for its respective ligand. Non-limiting examples of specific binding includes antibody-antigen binding, enzyme-substrate binding, enzyme-cofactor binding, metal ion chelation, DNA binding protein-DNA binding, regulatory protein-protein interactions, and the like. Ideally, in affinity chromatography specific binding occurs with an affinity of about $10^{-4}$ to $10^{-8}$ M in free solution.

The term "non-specific binding" as used herein, such as to describe interactions between a molecule of interest and a ligand or other compound bound to a solid phase matrix, refers to binding of a protein of interest to the ligand or compound on a solid phase matrix through electrostatic forces, hydrogen bonding, hydrophobic forces, and/or van der Waals forces at an interaction site, but lacking structural complementarity that enhances the effects of the non-structural forces. Examples of non-specific interactions include, but are not limited to, electrostatic, hydrophobic, and van der Waals forces as well as hydrogen bonding.

A "salt" is a compound formed by the interaction of an acid and a base. A salt useful for the invention include, but are not limited to acetate (e.g. sodium acetate), citrate (e.g. sodium citrate), chloride (e.g. sodium chloride), sulphate (e.g. sodium sulphate), or a potassium salt.

As used herein, "solvent" refers to a liquid substance capable of dissolving or dispersing one or more other substances to provide a solution. Solvents include aqueous and organic solvents, where useful organic solvents include a non-polar solvent, ethanol, methanol, isopropanol, acetonitrile, hexylene glycol, propylene glycol, and 2,2-thiodiglycol.

The term "detergent" refers to ionic and nonionic surfactants such as polysorbates (e.g. polysorbates 20 or 80); poloxamers (e.g. poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl oleyl-taurate; and the MONAQUAT™ series (Mona Industries, Inc., Paterson, N.J.), Useful detergents is a polysorbate, such as polysorbate 20 (TWEEN 20®) or polysorbate 80 (TWEEN 80®).

A "polymer" herein is a molecule formed by covalent linkage of two or more monomers, where the monomers are not amino acid residues. Examples of polymers include polyethyl glycol, polypropyl glycol, and copolymers (e.g. Pluronics, PF68 etc). A useful polymer is polyethylene glycol (PEG), e.g. PEG 400 and PEG 8000.

The term "ion-exchange" and "ion-exchange chromatography" refers to the chromatographic process in which a solute of interest (such as a protein) in a mixture interacts with a charged compound linked (such as by covalent attachment) to a solid phase ion exchange material such that the solute of interest interacts non-specifically with the charged compound more or less than solute impurities or contaminants in the mixture. The contaminating solutes in the mixture elute from a column of the ion exchange material faster or slower than the solute of interest or are bound to or excluded from the resin relative to the solute of interest. "Ion-exchange chromatography" specifically includes cation exchange, anion exchange, and mixed mode chromatography.

The phrase "ion exchange material" refers to a solid phase that is negatively charged (i.e. a cation exchange resin) or positively charged (i.e. an anion exchange resin). The charge may be provided by attaching one or more charged ligands to the solid phase, e.g. by covalent linking. Alternatively, or in addition, the charge may be an inherent property of the solid phase (e.g. as is the case for silica, which has an overall negative charge).

By "solid phase" is meant a non-aqueous matrix to which one or more charged ligands can adhere. The solid phase may be a purification column, a discontinuous phase of discrete particles, a membrane, or filter etc. Examples of materials for forming the solid phase include polysaccharides (such as agarose and cellulose); and other mechanically stable matrices such as silica (e.g. controlled pore glass), poly(styrenedivinyl)benzene, polyacrylamide, ceramic particles and derivatives of any of the above.

A "cation exchange resin" refers to a solid phase which is negatively charged, and which thus has free cations for exchange with cations in an aqueous solution passed over or through the solid phase. A negatively charged ligand attached to the solid phase to form the cation exchange resin may, e.g., be a carboxylate or sulfonate. Commercially available cation exchange resins include carboxy-methyl-cellulose, sulphopropyl (SP) immobilized on agarose (e.g. SP-SEPHAROSE FAST FLOW™ or SP-SEPHAROSE HIGH PERFORMANCE™, from Pharmacia) and sulphonyl immobilized on agarose (e.g. S-SEPHAROSE FAST FLOW™ from Pharmacia). A "mixed mode ion exchange resin" refers to a solid phase which is covalently modified with cationic, anionic, and hydrophobic moieties. A commercially available mixed mode ion exchange resin is BAKERBOND ABX™ (J. T. Baker, Phillipsburg, N.J.) containing weak cation exchange groups, a low concentration of anion exchange groups, and hydrophobic ligands attached to a silica gel solid phase support matrix.

The term "anion exchange resin" is used herein to refer to a solid phase which is positively charged, e.g. having one or more positively charged ligands, such as quaternary amino groups, attached thereto. Commercially available anion exchange resins include DEAE cellulose, QAE SEPHADEX™ and FAST Q SEPHAROSE™ (Pharmacia).

A "buffer" is a solution that resists changes in pH by the action of its acid-base conjugate components. Various buffers which can be employed depending, for example, on the desired pH of the buffer are described in *Buffers. A Guide for the Preparation and Use of Buffers in Biological Systems*, Gueffroy, D., ed. Calbiochem Corporation (1975). In one embodiment, the buffer has a pH in the range from about 2 to about 9, alternatively from about 3 to about 8, alternatively from about 4 to about 7 alternatively from about 5 to about 7. Non-limiting examples of buffers that will control the pH in this range include MES, MOPS, MOPSO, Tris, HEPES, phosphate, acetate, citrate, succinate, and ammonium buffers, as well as combinations of these.

The "loading buffer" is that which is used to load the composition comprising the polypeptide molecule of interest and one or more impurities onto the ion exchange resin. The loading buffer has a conductivity and/or pH such that the polypeptide molecule of interest (and generally one or more impurities) is/are bound to the ion exchange resin or such that the protein of interest flows through the column while the impurities bind to the resin.

The "intermediate buffer" is used to elute one or more impurities from the ion exchange resin, prior to eluting the polypeptide molecule of interest. The conductivity and/or pH of the intermediate buffer is/are such that one or more impurity is eluted from the ion exchange resin, but not significant amounts of the polypeptide of interest.

The term "wash buffer" when used herein refers to a buffer used to wash or re-equilibrate the ion exchange resin, prior to eluting the polypeptide molecule of interest. Conveniently, the wash buffer and loading buffer may be the same, but this is not required.

The "elution buffer" is used to elute the polypeptide of interest from the solid phase. The conductivity and/or pH of the elution buffer is/are such that the polypeptide of interest is eluted from the ion exchange resin.

A "regeneration buffer" may be used to regenerate the ion exchange resin such that it can be re-used. The regeneration buffer has a conductivity and/or pH as required to remove substantially all impurities and the polypeptide of interest from the ion exchange resin.

The term "conductivity" refers to the ability of an aqueous solution to conduct an electric current between two electrodes. In solution, the current flows by ion transport. Therefore, with an increasing amount of ions present in the aqueous solution, the solution will have a higher conductivity. The unit of measurement for conductivity is milliSeimens per centimeter (mS/cm), and can be measured using a conductivity meter sold, e.g., by Orion. The conductivity of a solution may be altered by changing the concentration of ions therein. For example, the concentration of a buffering agent and/or concentration of a salt (e.g. NaCl or KCl) in the solution may be altered in order to achieve the desired conductivity. Preferably, the salt concentration of the various buffers is modified to achieve the desired conductivity as in the Example below.

The "pI" or "isoelectric point" of a polypeptide refer to the pH at which the polypeptide's positive charge balances its negative charge. pI can be calculated from the net charge of the amino acid residues or sialic acid residues of attached carbohydrates of the polypeptide or can be determined by isoelectric focusing.

By "binding" a molecule to an ion exchange material is meant exposing the molecule to the ion exchange material under appropriate conditions (pH/conductivity) such that the molecule is reversibly immobilized in or on the ion exchange material by virtue of ionic interactions between the molecule and a charged group or charged groups of the ion exchange material.

By "washing" the ion exchange material is meant passing an appropriate buffer through or over the ion exchange material.

To "elute" a molecule (e.g. polypeptide or impurity) from an ion exchange material is meant to remove the molecule therefrom by altering the ionic strength of the buffer surrounding the ion exchange material such that the buffer competes with the molecule for the charged sites on the ion exchange material.

As used herein, "filtrate" refers to that portion of a sample that passes through the filtration membrane.

As used herein, "retentate" refers to that portion of a sample that is substantially retained by the filtration membrane.

Tangential flow filtration" or "TFF" or "crossflow filtration" refers to a filtration process in which the sample mixture circulates across the top of the membrane, while applied pressure causes certain solutes and small molecules to pass through the membrane. Typically, the solution flows parallel to the filter membrane. A pressure differential across the membrane causes fluid and filterable solutes to flow through the filter. This can be conducted as a continuous-flow process, since the solution is passed repeatedly over the membrane while that fluid that passes through the filter is continually drawn off into a separate circuit.

"High performance tangential flow filtration" or "HPTFF" refers to TFF performed at a flux between 5% and 100% of the transmembrane pressure on the flux versus transmembrane pressure curve (see, for example, van Reis, R. U.S. Pat. No. 5,256,694; U.S. Pat. No. 4,490,937; and U.S. Pat. No. 6,054,051).

As used herein, "lysate impurities" refers to all undesired components of a mixture in which the desired plasmid DNA is contained, including chromosomal DNA, host proteins, cell debris, secreted host cell proteins, including cell membrane debris, carbohydrates, small degraded nucleotides, host RNA, lipopolysaccharides, etc.

"Cellulose membrane" refers to a cellulose polymer, where the cellulose is repeating units of D-glucose. The primary alcohol group of a glucose monomer provides the reactive species on the membrane to which the charged compound is covalently attached.

"CRC membrane" refers to a composite regenerated cellulose membrane prepared by casting cellulose on a microporous substrate to control the average pore size and limit the number of defects in the cellulose sheet.

"Charged compound" refers to the compound linked to the filtration membrane, wherein the compound comprises a moiety having a positive or negative charge under the conditions used to separate a protein from a mixture of proteins. According to the invention, the charged compound may further comprise a linker arm between the membrane and the charged moiety such that the charged compound projects from the surface of the membrane. Where the charged compound projects from the surface of a pore into the lumen of the pore, the charged compound modifies the effective size of the pore and modifies the pore size distribution of the membrane.

"Reactive charged compound" refers to the charged compound prior to linkage to the membrane, such that the reactive charged compound still retains the reactive moiety that promotes the membrane-reactive charged compound reaction. For example, where the charged compound is a propyl trimethyl ammonium ion covalently attached to a cellulose membrane, the reactive charged compound may be bromopropyl trimethyl ammonium bromide. The covalent attachment involves nucleophilic displacement of the alkyl bromine by a primary alcohol of the cellulose matrix.

"Linker arm" refers to the portion of the charged compound molecule between the portion that reacts or has reacted with a reactive group on the surface of a filtration membrane and the charged moiety. Preferably, the linker arm is a chain of atoms or molecular subunits, which chain is inert to the reaction conditions used to covalently link the charged compound to the membrane, and is further inert to the aqueous conditions used during protein separation. A linker arm may comprise, but is not limited to, an alkyl chain of from one to twenty carbon atoms, a carbohydrate chain of from one to fifteen saccharide moities (including, for example, ribose and deoxyribose), a dextran chain of from one to fifteen saccharide moities, an amino acid chain of from one to twenty five amino acids, and other polymers (such as those used to manufacture the membrane itself) of from one to twenty five repeat units. Where a charged compound comprises an amino acid chain as a linker arm and the charged moiety is the terminal amino acid of the chain, the side chain of the terminal amino acid is preferably a charged side chain.

"Sieving" refers to the ratio of the concentration of a particular solute in the filtrate (downstream of the membrane) to the concentration of the same solute in the feed solution (upsteam of the membrane) (see Zeman and Zydney, supra, p. 308). Generally a high sieving value suggests that the solute readily passes through the membrane, while a low sieving value suggests that the solute is largely retained by the membrane. Where it is desired to retain a solute upstream of the membrane, a reduced sieving coefficient is preferred.

"Permeability" refers to the filtration rate divided by the net pressure drop across the membrane. Permeability is therefore the inverse of membrane resistance. Membrane permeability is primarily determined by pore size distribution, porosity (pore density), membrane thickness, and solvent viscosity. Generally, as permeability increases, sieving increases. When sieving is improved due to the addition of a charged compound to the membrane, the sieving improvement is an improvement relative to a membrane having substantially the same permeability as the charged membrane, but lacking the charged compound. Thus, where the improvement is a reduction in sieving because a charged solute, such as a protein, is retained by a like-charged membrane, the sieving is a reduction at comparable or substantially the same permeability. Consequently, the rate of filtration is maintained, while the selectivity of the membrane is improved.

"Pore size distribution" refers, basically, to the number of pores having an actual radius, R, near some theoretical radius, r, expressed as the probability density function (see, Zeman, L. J. and Zydney, A. L., supra, p. 299-301). As the standard deviation of actual pore radii increases, the pore size distribution increases. Narrowed pore size distribution results from a reduction in the standard deviation of the pores from the theoretical value. This is achieved, for example, when the sizes of some of the larger pores are reduced by addition of charged compound into the larger pores of a charged membrane. The principle of liquid-liquid pore intrusion is useful for measuring pore size distribution (see R. van Reis and A. L. Zydney, supra, p. 2201). According to this principle, two highly immiscible liquids, such as solutions of a sulfate salt and a poly(ethylene glycol) are contacted through mixing to reach equilibrium partitioning. The membrane to be tested is primed with one of the liquids so that all pores are filled. After draining the feed channels, the second fluid is introduced into the system. The first fluid is then displaced out of the pores by the second fluid, and the flow rate is measured as a function of trans-membrane pressure. The resulting data provide information on pore size distribution and can be correlated with the nominal molecular weight cutoff (see R. van Reis and A. L. Zydney, supra, p. 2201).

"Net charge" when referring to a membrane or protein charge is meant a charge that is predominately positive or negative, but does not refer to a specific value for the number of positive charges versus the number of negative charges on the membrane or protein, unless otherwise noted. Similarly, "like charge" and "same charge" refer to the situation in which a protein having a given charge, positive or negative, is compared to a membrane or other protein having a given charge, either positive or negative.

"Treatment" refers to both therapeutic treatment and prophylactic or preventative measures. Those in need of treatment include those already with the disorder as well as those in which the disorder is to be prevented.

A "disorder" is any condition that would benefit from treatment with the polypeptide purified as described herein. This includes chronic and acute disorders or diseases including those pathological conditions which predispose the mammal to the disorder in question.

The word "label" when used herein refers to a detectable compound or composition which is conjugated directly or indirectly to the polypeptide. The label may itself be detectable (e.g., radioisotope labels or fluorescent labels) or, in the case of an enzymatic label, may catalyze chemical alteration of a substrate compound or composition which is detectable.

B. Modes for Carrying Out the Invention

1. Protein Purification

Manufacturers of protein-based pharmaceutical products must comply with strict regulatory standards, including extremely stringent purity requirements. To ensure safety, regulatory agencies, such as the Food and Drug Administration (FDA), require that protein-based pharmaceuticals, including those produced by recombinant DNA technology, be substantially free from impurities, such as host cell proteins, viruses, DNA, endotoxins, aggregates, fragments, and variants of the recombinant protein, and the like. While various protein purification protocols are available and widely used in the pharmaceutical industry, they typically include affinity-purification, such as Protein A purification in the case of antibodies, in order to reach the required degree of purity. As indicated herein above, although Protein A affinity removes more than 99.5% of impurities, this benefit comes at a price. Protein A is significantly more expensive than the price of non-affinity media, and Protein A-based purification methods often raise issues associated with resin stability, cleanability and lifetime, ligand leakage, and the potential immunogenicity of Protein A residues contaminating the purified product.

The present invention involves the purification of proteins, in particular recombinant proteins, by a protocol not including an affinity chromatography step. More specifically, the invention provides methods for the purification of (recombinant) proteins, including but not limited to antibodies, by steps not including affinity chromatography, to a degree that allows direct use of the purified proteins in human therapy, thereby eliminating costly affinity chromatography steps as well as a final ultrafiltration diafiltration frequently required to concentration and formulate a therapeutic protein.

The present invention is based on experimental findings demonstrating that recombinant proteins can be purified from a mixture comprising host cell proteins by purification schemes not employing affinity chromatography to the same degree as processes incorporating an affinity chromatography step. In particular, it was found that a three-step non-affinity purification process, including two non-affinity chromatography steps followed by high performance tangential flow filtration (HPTFF) as the last step, can yield a high-purity product that contains host cell protein impurities in an amount less than 100 parts per million (ppm).

The protein to be purified using the method described herein is generally produced using recombinant techniques.

Methods for producing recombinant proteins are described, e.g., in U.S. Pat. Nos. 5,534,615 and 4,816,567, specifically incorporated herein by reference. In preferred embodiments, the protein of interest is produced in a CHO cell (see, e.g. WO 94/11026). Examples of proteins which can be purified using the process described herein have been described above.

When using recombinant techniques, the protein can be produced intracellularly, in the periplasmic space, or directly secreted into the medium. If the protein is produced intracellularly, as a first step, the particulate debris, either host cells or lysed fragments, is removed, for example, by centrifugation or filtration. Where the protein is secreted into the medium, the recombinant host cells may be separated from the cell culture medium by tangential flow filtration, for example.

Once a mixture containing the protein of interest has been obtained, its separation from the other proteins produced by the cell is usually performed using a combination of different chromatography techniques. These techniques separate mixtures of proteins on the basis of their charge, degree of hydrophobicity, or size. Several different chromatography resins are available for each of these techniques, allowing accurate tailoring of the purification scheme to the particular protein involved. The essence of each of these separation methods is that proteins can be caused either to move at different rates down a long column, achieving a physical separation that increases as they pass further down the column, or to adhere selectively to the separation medium, being then differentially eluted by different buffers. In some cases, the desired protein is separated from impurities when the impurities specifically adhere to the column, and the protein of interest does not, that is, the protein of interest is present in the "flow-through".

As noted before, according to the present invention, proteins can be purified to a degree characterized by the presence of less than 100 ppm host cell protein impuritites by one or two non-affinity purification steps, followed by HPTFF. The non-affinity purification steps may be based on non-affinity chromatography, or may include non-chromatographic purification techniques.

Exemplary non-affinity chromatography purification steps include hydroxyapatite chromatography; hydrophobic interaction chromatography (HIC); reverse phase HPLC; chromatography on silica; chromatofocusing; and gel filtration; cation exchange (e.g., SP-Sepharose) chromatography; anion exchange (e.g., Q-Sepharose) chromatography, mixed mode chromatography (e.g., ABx), and hydrophobic charge induction chromatography.

Exemplary non-affinity, non-chromatographic purification steps include dialysis; ammonium sulphate precipitation; and ethanol precipitation.

In a preferred embodiment, the process of the present invention includes two chromatographic non-affinity separation steps, followed by HPTTF, optionally charged membrane HPTFF. In another preferred embodiment, the chromatographic non-affinity separation steps are selected from cation exchange chromatography, anion exchange chromatography, mixed mode ion exchange chromatography, hydrophobic interaction chromatography (HIC), and hydrophobic charge induction chromatography (HCI). In another preferred embodiment, the purification protocol includes the steps of (1) cation exchange chromatography, (2) anion exchange chromatography, and (3) HPTFF in this order, in the absence of any affinity purification steps, and, preferably, without further purification steps of any kind.

Ion exchange chromatography is a chromatographic technique that is commonly used for the purification of proteins. In ion exchange chromatography, charged patches on the surface of the solute are attracted by opposite charges attached to a chromatography matrix, provided the ionic strength of the surrounding buffer is low. Elution is generally achieved by increasing the ionic strength (i.e. conductivity) of the buffer to compete with the solute for the charged sites of the ion exchange matrix. Changing the pH and thereby altering the charge of the solute is another way to achieve elution of the solute. The change in conductivity or pH may be gradual (gradient elution) or stepwise (step elution). In the past, these changes have been progressive; i.e., the pH or conductivity is increased or decreased in a single direction.

The impure preparation derived from the recombinant host cells is loaded on the equilibrated chromatography solid phase matrix using a loading buffer which may be the same as the equilibration buffer. As the impure preparation flows through the solid phase, the protein and other impurities (such as Chinese Hamster Ovary Proteins, CHOP, where the protein is produced in a CHO cell) bind differentially to the solid phase thereby effecting separation as the proteins pass through the chromatography column.

The amount and type of buffer, salt, and/or other compound in the buffer composition are such that the combined amount elutes the protein impurity(ies) differentially from the protein of interest, where the protein of interest may be retained relative to the impurities or the impurities are retained relative to the protein of interest. Buffers salts and other additives useful in practicing the invention include without limitation buffer salts such as acetate, citrate, histidine, phosphate, ammonium acetate, MES, CHAPS, MOPSO, Tris, and the like; salts for adjusting buffer ionic strength such as sodium chloride and potassium chloride; and other additives such as amino acids (such as glycine and histidine), chaotropes (such as urea), alcohols (such as ethanol, mannitol, glycerol, and benzyl alcohol), detergent (such as Tween™ and C12E8), and sugars (such as sucrose, mannitol, maltose, trehalose, glucose, and fructose). Any of these buffers and additives and the concentrations used may vary according to the type of chromatography practiced, which buffer and additive compositions and concentrations are readily determined by standard methods.

The pH of the elution buffer may be from about 2 to about 9, alternatively from about 3 to about 8, from about 4 to about 8, or from about 5 to about 8, although the pH or pH range for elution will be determined according to the protein of interest and the type of chromatography and HPTFF practiced. Appropriate pH ranges for a loading, wash, or elution buffer are readily determined by standard methods such that the protein of interest is recovered in an active form. Examples of elution buffers for this purpose include citrate or acetate buffers.

The ionic strength of a buffer (measured as conductivity, for example) may be from about 0.2-20 mS/cm, alternatively from about 0.2-8 mS/cm, from about 0.2-6 mS/cm, from about 0.2-4 mS/cm, from about 0.2-2 mS/cm, or from about 1-2 mS/cm, although the ionic strength or ionic strength range for a load, wash, or elution buffer will be determined according to the protein of interest and the type of chromatography practiced and diafiltration buffers for the HPTFF method practiced. Appropriate ionic strength ranges for a buffer are readily determined by standard methods such that the protein of interest is recovered in an active form.

The cation exchange chromatography step typically removes at least part of the host cell proteins, e.g. CHOP, if the protein was produced in CHO cells, and variants, degradation products, and aggregates of the protein to be purified. The anion exchange chromatography step further purifies the protein from the remaining host cell proteins, e.g. CHOP, variants, degradation products, and aggregates of the protein, and also from endotoxins and DNA impurities.

Following non-affinity chromatography or other non-affinity purification, the eluted protein of interest is subject to HPTFF. HPTFF is a two-dimensional unit operation that selectively separates solutes on the basis of both size and charge. HPTFF is able to provide the high selectivity required for effective protein purification by exploiting several recent developments. First, unlike traditional membrane processes, HPTFF is operated in the pressure-dependent regime under conditions to minimize fouling, exploit concentration polarization, optimize separation by maintaining a nearly uniform flux and transmembrane pressure throughout the separation module (van Reis, R., U.S. Pat. Nos. 5,256,694; 5,490,937; and 6,054,051, supra). Separation selectivity can be improved by controlling filtrate buffer pH and ionic strength to maximize differences in effective volume of the different species in a mixture van Reis et al. (1997), supra; and Saksena, S. and Zydney, A. L., Biotechnol. Bioeng 43:960-968 (1994). In addition, the electrical charge of the membrane can be modified to increase the electrostatic exclusion of all species with like charge. Thus, a positively charged membrane will reject a positively charged protein to a greater extent than a negatively charged membrane of a similar pore size (van Reis et al., (2001) supra; Nakao, S. et al., Desalination 70:191-205 (1988); and van Reis et al., J. Membr. Sci. 159:133-142 (1999). Further, protein separations in HPTFF are accomplished using a diafiltration mode in which the impurity (or product) is washed out of the retentate by simultaneously adding fresh buffer to the feed reservoir as filtrate is removed through the membrane. This buffer addition maintains an appropriate protein concentration in the retentate throughout the separation. Diafiltration also makes it possible to obtain purification factors for products collected in the retentate that are greater than the membrane selectivity due to the continual removal of impurities in the filtrate (van Reis et al., (2001) supra; and van Reis, R. and Saksena, S., J. Membr. Sci. 129:19-29 (1997)).

An HPTFF filtration membrane useful for protein separations is a synthetic (frequently polymeric) selective barrier for industrial or lab-scale ultrafiltration (UF) (see Leos J. Zeman and Andrew L. Zydney, "Microfiltration and Ultrafiltration: Principles and Applications," 1996, Marcel Dekker, Inc., p. 3). In these processes, certain feed stream components, such as proteins, pass through pores of the membrane into a filtrate, while other, usually larger, proteins or components are retained by the membrane in the retentate (see Zeman and Zydney, supra, p. 3).

Protein ultrafiltration is a pressure-driven membrane process used for the concentration or purification of protein solutions (Robert van Reis and Andrew L. Zydney, "Protein Ultrafiltration" in *Encyclopedia of Bioprocess Technology: Fermentation, Biocatalysis, and Bioseparation*, M. C. Flickinger and S. W. Drew, eds., John Wiley & Sons, Inc. (1999), p. 2197). UF membranes typically have a mean pore size between 10 and 500 Angstroms, which is between the mean pore size of reverse osmosis and microfiltration membranes. Ultrafiltration separates solutes based on differences in the rate of filtration of different components across the membrane in response to a given pressure driving force (R. van Reis and A. L. Zydney, supra, p. 2197). Solute filtration rates, and thus membrane selectivity, are determined by both thermodynamic and hydrodynamic interactions (R. van Reis and A. L. Zydney, supra, p. 2197). Ultrafiltration is frequently used in downstream processing for protein concentration, buffer exchange and desalting, protein purification, virus clearance, and clarification (R. van Reis and A. L. Zydney, supra, p. 2197).

Using HPTFF, the desired protein is collected in either the retentate or filtrate depending on the relative filtration rates (R. van Reis and A. L. Zydney, supra, p. 2197). HPTFF is useful for separating proteins of similar size using the above-described semipermeable membranes (See, for example, R. van Reis, et al., Biotech. Bioeng. 56:71-82 (1997) and R. van Reis et al., J. Memb. Sci. 159:133-142 (1999)). HPTFF achieves high selectivity by controlling filtrate flux and device fluid mechanics in order to minimize fouling and exploit the effects of concentration polarization (R. van Reis et al., J. Memb. Sci. 159:133-142 (1999)).

The performance of HPTFF can be evaluated by two parameters, selectivity and throughput, which are used to optimize process yield and purification factor (van Reis and Saksena, supra, 1997; van Reis et al., supra, 1999). The selectivity is defined as the ratio of the observed sieving coefficients of the permeable and retained solutes. Since the present HPTFF application is based on the retention of a target protein and the sieving of HCP, or impurities, the selectivity is described as:

$$\Psi = \frac{S_{HCP}}{S_{Targetprotein}} \quad \text{Equation 1}$$

where the sieving coefficient is defined as the dimensionless ratio:

$$S = \frac{C_{filtrate}}{C_{Feed}} \quad \text{Equation 2}$$

with $C_{filtrate}$ and $C_{feed}$ the solute concentrations in the filtrate and in the feed lines.

The throughput is defined as the product of the filtrate flux and the difference in sieving between the permeable and retained solutes:

$$J \cdot \Delta S = J \cdot (S_{HCP} - S_{Target\,protein}) \quad \text{Equation 3}$$

Another calculated process parameter is the retentate yield during constant volume diafiltration. This yield is expressed as:

$$Y = e^{-N S_{targetprotein}} \quad \text{Equation 4}$$

where N equals the number of diavolumes and S equals the sieving of the considered solute.

Further details of the HPTFF purification steps will be provided in the Examples below.

The preferred measure of protein purification by the process of the present invention is the measure of host cell protein impurity, e.g. CHOP impurity, where the recombinant protein to be purified is produced in CHO cells. The purified protein preferably should contain less than 100, more preferably less than 90, less than 80, less than 70, less than 60, less than 50, less than 40, less than 30, less than 20, less than 10, less than 5 ppm, or less than 3 ppm of host cell proteins, e.g. CHOP, where the ppm values are calculated as defined above.

The protein thus recovered may be formulated in a pharmaceutically acceptable carrier and is used for various diagnostic, therapeutic or other uses known for such molecules.

2. Antibodies

The preferred protein to be purified according to the present invention is an antibody. In particular, as described in the Examples below, for purification of recombinant humanized monoclonal antibody (RhuMAb), conditioned Harvested Cell Culture Fluid (HCCF) from chinese hamster ovary (CHO) cells expressing RhuMAb was loaded onto an initial cation exchange column (SP-Sepharose Fast Flow Resin, Amersham Biosciences; (S)). The material collected from the S column, the S pool, was collected from the SP-Sepharose column, conditioned and then loaded onto an anion exchange (Q-Sepharose Fast Flow resin, Amersham Biosciences; (Q)). The material collected from the anion exchange column (such as the Q column, as each the Q pool) was further purified by HPTFF.

Antibodies within the scope of the present invention include, but are not limited to: anti-HER2 antibodies including Trastuzumab (HERCEPTIN®) (Carter et al., *Proc. Natl. Acad. Sci. USA*, 89:4285-4289 (1992), U.S. Pat. No. 5,725, 856); anti-CD20 antibodies such as chimeric anti-CD20 "C2B8" as in U.S. Pat. No. 5,736,137 (RITUXAN®), a chimeric or humanized variant of the 2H7 antibody as in U.S. Pat. No. 5,721,108, B1, or Tositumomab (BEXXAR®); anti-IL-8 (St John et al., *Chest*, 103:932 (1993), and International Publication No. WO 95/23865); anti-VEGF antibodies including humanized and/or affinity matured anti-VEGF antibodies such as the humanized anti-VEGF antibody huA4.6.1 AVASTIN® (Kim et al., *Growth Factors*, 7:53-64 (1992), International Publication No. WO 96/30046, and WO 98/45331, published Oct. 15, 1998); anti-PSCA antibodies (WO01/40309); anti-CD40 antibodies, including S2C6 and humanized variants thereof (WO00/75348); anti-CD11a (U.S. Pat. No. 5,622,700, WO 98/23761, Steppe et al., *Transplant Intl.* 4:3-7 (1991), and Hourmant et al., *Transplantation* 58:377-380 (1994)); anti-IgE (Presta et al., *J. Immunol.* 151:2623-2632 (1993), and International Publication No. WO 95/19181); anti-CD18 (U.S. Pat. No. 5,622,700, issued Apr. 22, 1997, or as in WO 97/26912, published Jul. 31, 1997); anti-IgE (including E25, E26 and E27; U.S. Pat. No. 5,714,338, issued Feb. 3, 1998 or U.S. Pat. No. 5,091,313, issued Feb. 25, 1992, WO 93/04173 published Mar. 4, 1993, or International Application No. PCT/US98/13410 filed Jun. 30, 1998, U.S. Pat. No. 5,714,338); anti-Apo-2 receptor antibody (WO 98/51793 published Nov. 19, 1998); anti-TNF-α antibodies including cA2 (REMICADE®), CDP571 and MAK-195 (See, U.S. Pat. No. 5,672,347 issued Sep. 30, 1997, Lorenz et al. *J. Immunol.* 156(4):1646-1653 (1996), and Dhainaut et al. *Crit. Care Med.* 23(9):1461-1469 (1995)); anti-Tissue Factor (TF) (European Patent No. 0 420 937 B1 granted Nov. 9, 1994); anti-human $\alpha_4\beta_7$ integrin (WO 98/06248 published Feb. 19, 1998); anti-EGFR (chimerized or humanized 225 antibody as in WO 96/40210 published Dec. 19, 1996); anti-CD3 antibodies such as OKT3 (U.S. Pat. No. 4,515,893 issued May 7, 1985); anti-CD25 or anti-tac antibodies such as CHI-621 (SIMULECT®) and (ZENAPAX®) (See U.S. Pat. No. 5,693,762 issued Dec. 2, 1997); anti-CD4 antibodies such as the cM-7412 antibody (Choy et al. *Arthritis Rheum* 39(1):52-56 (1996)); anti-CD52 antibodies such as CAMPATH-1H (Riechmann et al. *Nature* 332:323-337 (1988)); anti-Fc receptor antibodies such as the M22 antibody directed against FcγRI as in Graziano et al. *J. Immunol.* 155(10):4996-5002 (1995); anti-carcinoembryonic antigen (CEA) antibodies such as hMN-14 (Sharkey et al. *Cancer Res.* 55(23Suppl): 5935s-5945s (1995); antibodies directed against breast epithelial cells including huBrE-3, hu-Mc 3 and CHL6 (Ceriani et al. *Cancer Res.* 55(23): 5852s-5856s (1995); and Richman et al. Cancer Res. 55(23 Supp): 5916s-5920s (1995)); antibodies that bind to colon carcinoma cells such as C242 (Litton et al. Eur J. Immunol. 26(1):1-9 (1996)); anti-CD38 antibodies, e.g. AT 13/5 (Ellis et al. *J. Immunol.* 155(2):925-937 (1995)); anti-CD33 antibodies such as Hu M195 (Jurcic et al. *Cancer Res* 55(23 Suppl):5908s-5910s (1995) and CMA-676 or CDP771; anti-CD22 antibodies such as LL2 or LymphoCide (Juweid et al. *Cancer Res* 55(23 Suppl):5899s-5907s (1995)); anti-Ep-CAM antibodies such as 17-1A (PANOREX®); anti-GpIIb/IIIa antibodies such as abciximab or c7E3 Fab (REOPRO®); anti-RSV antibiodies such as MEDI-493 (SYNAGIS®); anti-CMV antibodies such as PROTOVIR®; anti-HIV antibodies such as PRO542; anti-hepatitis antibodies such as the anti-Hep B antibody OSTAVIR®; anti-CA 125 antibody OvaRex; anti-idiotypic GD3 epitope antibody BEC2; anti-αvβ3 antibody VITAXIN®; anti-human renal cell carcinoma antibody such as ch-G250; ING-1; anti-human 17-1A antibody (3622W94); anti-human colorectal tumor antibody (A33); anti-human melanoma antibody R24 directed against GD3 ganglioside; anti-human squamous-cell carcinoma (SF-25); and anti-human leukocyte antigen (HLA) antibodies such as Smart ID10 and the anti-HLA DR antibody Oncolym (Lym-1). The preferred target antigens for the antibody herein are: HER2 receptor, VEGF, IgE, CD20, CD11a, and CD40.

Aside from the antibodies specifically identified above, the skilled practitioner could generate antibodies directed against an antigen of interest, e.g., using the techniques described below.

(a) Antigen Selection and Preparation

The antibody herein is directed against an antigen of interest. Preferably, the antigen is a biologically important polypeptide and administration of the antibody to a mammal suffering from a disease or disorder can result in a therapeutic benefit in that mammal. However, antibodies directed against nonpolypeptide antigens (such as tumor-associated glycolipid antigens; see U.S. Pat. No. 5,091,178) are also contemplated. Where the antigen is a polypeptide, it may be a transmembrane molecule (e.g. receptor) or ligand such as a growth factor. Exemplary antigens include those proteins described in section (3) below. Exemplary molecular targets for antibodies encompassed by the present invention include CD proteins such as CD3, CD4, CD8, CD19, CD20, CD22, CD34, CD40; members of the ErbB receptor family such as the EGF receptor, HER2, HER3 or HER4 receptor; cell adhesion molecules such as LFA-1, Mac1, p150,95, VLA-4, ICAM-1, VCAM and αv/β3 integrin including either α or β subunits thereof (e.g. anti-CD11a, anti-CD18 or anti-CD11b antibodies); growth factors such as VEGF; IgE; blood group antigens; flk2/flt3 receptor; obesity (OB) receptor; mpl receptor; CTLA-4; protein C, or any of the other antigens mentioned herein. Antigens to which the antibodies listed above bind are specifically included within the scope herein.

Soluble antigens or fragments thereof, optionally conjugated to other molecules, can be used as immunogens for generating antibodies. For transmembrane molecules, such as receptors, fragments of these (e.g. the extracellular domain of a receptor) can be used as the immunogen. Alternatively, cells expressing the transmembrane molecule can be used as the immunogen. Such cells can be derived from a natural source (e.g. cancer cell lines) or may be cells which have been transformed by recombinant techniques to express the transmembrane molecule.

Other antigens and forms thereof useful for preparing antibodies will be apparent to those in the art.

(b) Polyclonal Antibodies

Polyclonal antibodies are preferably raised in animals by multiple subcutaneous (sc) or intraperitoneal (ip) injections of the relevant antigen and an adjuvant. It may be useful to conjugate the antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later the animals are boosted with ⅕ to ⅒ the original amount of antigen or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

(c) Monoclonal Antibodies

Monoclonal antibodies may be made using the hybridoma method first described by Kohler et al., *Nature,* 256:495 (1975), or may be made by recombinant DNA methods (U.S. Pat. No. 4,816,567).

In the hybridoma method, a mouse or other appropriate host animal, such as a hamster or macaque monkey, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice,* pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.,* 133:3001 (1984); Brodeur et al., *Monoclonal Antibody Production Techniques and Applications,* pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice,* pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, Protein A-Sepharose, hydroxyapatite chromatography, gel electrophoresis, dialysis, or affinity chromatography. Preferably the Protein A chromatography procedure described herein is used.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells.

The DNA also may be modified, for example, by substituting the coding sequence for human heavy- and light-chain constant domains in place of the homologous murine sequences (U.S. Pat. No. 4,816,567; Morrison, et al., *Proc. Natl Acad. Sci. USA,* 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

In a further embodiment, monoclonal antibodies can be isolated from antibody phage libraries generated using the techniques described in McCafferty et al., *Nature,* 348:552-554 (1990). Clackson et al., *Nature,* 352:624-628 (1991) and Marks et al., *J. Mol. Biol.,* 222:581-597 (1991) describe the isolation of murine and human antibodies, respectively, using phage libraries. Subsequent publications describe the production of high affinity (nM range) human antibodies by chain shuffling (Marks et al., *Bio/Technology,* 10:779-783 (1992)), as well as combinatorial infection and in vivo recombination as a strategy for constructing very large phage libraries (Waterhouse et al., *Nuc. Acids. Res.,*

21:2265-2266 (1993)). Thus, these techniques are viable alternatives to traditional hybridoma techniques for isolation of monoclonal antibodies.

(d) Humanized and Human Antibodies

A humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321:522-525 (1986); Riechmann et al., *Nature*, 332:323-327 (1988); Verhoeyen et al., *Science*, 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human FR for the humanized antibody (Sims et al., *J. Immunol.*, 151:2296 (1993)). Another method uses a particular framework derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immnol.*, 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA*, 90:2551 (1993); Jakobovits et al., *Nature*, 362:255-258 (1993); Bruggermann et al., *Year in Immuno.*, 7:33 (1993); and Duchosal et al. *Nature* 355:258 (1992). Human antibodies can also be derived from phage-display libraries (Hoogenboom et al., *J. Mol. Biol.*, 227:381 (1991); Marks et al., *J. Mol. Biol.*, 222:581-597 (1991); Vaughan et al. *Nature Biotech* 14:309 (1996)).

(e) Antibody Fragments

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992) and Brennan et al., *Science*, 229:81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al., *Bio/Technology* 10:163-167 (1992)). According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185.

(e) Multispecific Antibodies

Multispecific antibodies have binding specificities for at least two different antigens. While such molecules normally will only bind two antigens (i.e. bispecific antibodies, BsAbs), antibodies with additional specificities such as trispecific antibodies are encompassed by this expression when used herein.

Methods for making bispecific antibodies are known in the art. Traditional production of full length bispecific antibodies is based on the coexpression of two immunoglobulin heavy chain-light chain pairs, where the two chains have different specificities (Millstein et al., *Nature*, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.*, 10:3655-3659 (1991).

According to another approach described in WO96/27011, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994). Alternatively, the antibodies can be "linear antibodies" as described in Zapata et al. *Protein Eng.* 8(10):1057-1062 (1995). Briefly, these antibodies comprise a pair of tandem Fd segments ($V_H$-$C_H$1-$V_H$-$C_H$1) which form a pair of antigen binding regions. Linear antibodies can be bispecific or monospecific.

Antibodies with more than two valencies are contemplated. For example, trispecific antibodies can be prepared. Tutt et al. *J. Immunol.* 147: 60 (1991).

3. Immunoadhesins

The simplest and most straightforward immunoadhesin design combines the binding domain(s) of the adhesin (e.g. the extracellular domain (ECD) of a receptor) with the hinge and Fc regions of an immunoglobulin heavy chain. Ordinarily, when preparing the immunoadhesins of the present invention, nucleic acid encoding the binding domain of the adhesin will be fused C-terminally to nucleic acid encoding the N-terminus of an immunoglobulin constant domain sequence, however N-terminal fusions are also possible.

Typically, in such fusions the encoded chimeric polypeptide will retain at least functionally active hinge, $C_H2$ and $C_H3$ domains of the constant region of an immunoglobulin heavy chain. Fusions are also made to the C-terminus of the Fc portion of a constant domain, or immediately N-terminal to the $C_H1$ of the heavy chain or the corresponding region of the light chain. The precise site at which the fusion is made is not critical; particular sites are well known and may be selected in order to optimize the biological activity, secretion, or binding characteristics of the immunoadhesin.

In a preferred embodiment, the adhesin sequence is fused to the N-terminus of the Fc domain of immunoglobulin $G_1$ (IgG$_1$). It is possible to fuse the entire heavy chain constant region to the adhesin sequence. However, more preferably, a sequence beginning in the hinge region just upstream of the papain cleavage site which defines IgG Fc chemically (i.e. residue 216, taking the first residue of heavy chain constant region to be 114), or analogous sites of other immunoglobulins is used in the fusion. In a particularly preferred embodiment, the adhesin amino acid sequence is fused to (a) the hinge region and $C_H2$ and $C_H3$ or (b) the $C_H1$, hinge, $C_H2$ and $C_H3$ domains, of an IgG heavy chain.

For bispecific immunoadhesins, the immunoadhesins are assembled as multimers, and particularly as heterodimers or heterotetramers. Generally, these assembled immunoglobulins will have known unit structures. A basic four chain structural unit is the form in which IgG, IgD, and IgE exist. A four chain unit is repeated in the higher molecular weight immunoglobulins; IgM generally exists as a pentamer of four basic units held together by disulfide bonds. IgA globulin, and occasionally IgG globulin, may also exist in multimeric form in serum. In the case of multimer, each of the four units may be the same or different.

Various exemplary assembled immunoadhesins within the scope herein are schematically diagrammed below:

(a) $AC_L$-$AC_L$;

(b) $AC_H$-($AC_H$, $AC_L$-$AC_H$, $AC_L$-$V_H C_H$, or $V_L C_L$-$AC_H$);

(c) $AC_L$-$AC_H$-($AC_L$-$AC_H$, $AC_L$-$V_H C_H$, $V_L C_L$-$AC_H$, or $V_L C_L$-$V_H C_H$)

(d) $AC_L$-$V_H C_H$-($AC_H$, or $AC_L$-$V_H C_H$, or $V_L C_L$-$AC_H$);

(e) $V_L C_L$-$AC_H$-($AC_L$-$V_H C_H$, or $V_L C_L$-$AC_H$); and (f) (A-Y)$_n$-($V_L C_L$-$V_H C_H$)$_2$, wherein each A represents identical or different adhesin amino acid sequences;

$V_L$ is an immunoglobulin light chain variable domain;
$V_H$ is an immunoglobulin heavy chain variable domain;
$C_L$ is an immunoglobulin light chain constant domain;
$C_H$ is an immunoglobulin heavy chain constant domain;
n is an integer greater than 1;
Y designates the residue of a covalent cross-linking agent.

In the interests of brevity, the foregoing structures only show key features; they do not indicate joining (J) or other domains of the immunoglobulins, nor are disulfide bonds shown. However, where such domains are required for binding activity, they shall be constructed to be present in the ordinary locations which they occupy in the immunoglobulin molecules.

Alternatively, the adhesin sequences can be inserted between immunoglobulin heavy chain and light chain sequences, such that an immunoglobulin comprising a chimeric heavy chain is obtained. In this embodiment, the adhesin sequences are fused to the 3' end of an immunoglobulin heavy chain in each arm of an immunoglobulin, either between the hinge and the $C_H2$ domain, or between the $C_H2$ and $C_H3$ domains. Similar constructs have been reported by Hoogenboom, et al., *Mol. Immunol.* 28:1027-1037 (1991).

Although the presence of an immunoglobulin light chain is not required in the immunoadhesins of the present invention, an immunoglobulin light chain might be present either covalently associated to an adhesin-immunoglobulin heavy chain fusion polypeptide, or directly fused to the adhesin. In the former case, DNA encoding an immunoglobulin light chain is typically coexpressed with the DNA encoding the adhesin-immunoglobulin heavy chain fusion protein. Upon secretion, the hybrid heavy chain and the light chain will be covalently associated to provide an immunoglobulin-like structure comprising two disulfide-linked immunoglobulin heavy chain-light chain pairs. Methods suitable for the preparation of such structures are, for example, disclosed in U.S. Pat. No. 4,816,567, issued Mar. 28, 1989.

Immunoadhesins are most conveniently constructed by fusing the cDNA sequence encoding the adhesin portion in-frame to an immunoglobulin cDNA sequence. However, fusion to genomic immunoglobulin fragments can also be used (see, e.g. Aruffo et al., *Cell* 61:1303-1313 (1990); and Stamenkovic et al., Cell 66:1133-1144 (1991)). The latter type of fusion requires the presence of Ig regulatory sequences for expression. cDNAs encoding IgG heavy-chain constant regions can be isolated based on published sequences from cDNA libraries derived from spleen or peripheral blood lymphocytes, by hybridization or by polymerase chain reaction (PCR) techniques. The cDNAs encoding the "adhesin" and the immunoglobulin parts of the immunoadhesin are inserted in tandem into a plasmid vector that directs efficient expression in the chosen host cells.

4. Other $C_H2/C_H3$ region-containing proteins

In other embodiments, the protein to be purified is one which is fused to, or conjugated with, a $C_H2/C_H3$ region. Such fusion proteins may be produced so as to increase the serum half-life of the protein. Examples of biologically important proteins which can be conjugated this way include renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; Protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins; CD proteins such as CD3, CD4, CD8, CD19, CD20, CD34, and CD40; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane. proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA-4 and VCAM; a tumor associated antigen such as HER2, HER3 or HER4 receptor; and fragments of any of the above-listed polypeptides.

The following examples are offered by way of illustration and not by way of limitation. The disclosures of all citations in the specification are expressly incorporated herein by reference.

EXAMPLES

The examples are provided so as to provide those of ordinary skill in the art with a complete disclosure and description of how to make and use the compounds, compositions, and methods of the invention and are not intended to limit the scope of what the inventors regard as their invention. Efforts have been made to insure accuracy with respect to numbers used (e.g. amounts, temperature, etc.) but has some experimental errors and deviation should be accounted for. The disclosures of all citations in the specification are expressly incorporated herein by reference.

For ease of reading, a list of abbreviations frequently used throughout the examples is provided below:
$C_f$ Concentration in the filtrate (g/l)
$C_b$ Bulk concentration (or feed concentration) (g/l)
CHO Chinese hamster ovary
CHOP Chinese hamster ovary cell protein(s)
CV Column volumes
DF Diafiltration
HCCF Harvested cell culture fluid HCI Hydrophobic charge induction chromatography
HCP Host cell protein(s)
HIC Hydrophobic interaction chromatography
HPLC High performance liquid chromatography
HPTFF High performance tangential flow filtration
J Filtrate flux ($lm^{-2}h^{-1}$)
Lp Membrane permeability
N Number of diavolumes
$P_{HCP}$ Purification factor based on HCP removal
$P_{CHOP}$ Purification factor based on CHOP removal
pI Isoelectric point
rhuMAb Recombinant humanized monoclonal antibody
$S_i$ Sieving of solute "i"
Y Yield
ψ Selectivity Example 1

Two Steps of Non-affinity Purification

In the present example, the purification of anti-CD11a rhuMAb HCCF was performed with processes consisting of either two steps of non-affinity purification or three steps of non-affinity purification using different combinations of non-affinity purification matrices.

The purification performance of cation exchange (such as by using an S column), anion exchange (such as by using a Q column), mixed-mode ion exchange (such as by using ABx), hydroxyapatite (HA), hydrophobic interaction (HIC) and hydrophobic charge induction (HCI) resins were examined in each step of the chromatographic purification process for the anti-CD11a rhuMAb protein. Total host cell protein (CHOP) impurity removal and protein yield was determined as described in detail in Example 2 and compared to traditional processes consisting of either two or three steps and incorporating Protein A chromatography (i.e. for two step processes, ProA followed by anion exchange (such as ProA-Q), and for three steps processes, ProA followed by cation exchange, then anion exchange, such as by ProA-S-Q).

SP-SEPHAROSE FAST FLOW™ resin (S, cation exchange resin, Amersham Biosciences, Piscataway, N.J.), Q-Sepharose Fast FLOW™ resin (Q, anion exchange resin, Amersham Biosciences, supra), Bakerbond ABX™ resin (ABx, mixed-mode ion exchange resin, J. T. Baker, Inc., Phillipsburg, N.J.), PHENYL-SEPHAROSE FAST FLOW™ resin (HIC, hydrophobic interaction resin, Amersham Biosciences, supra), Macroprep Ceramic Hydroxyapatite resin (HA, hydroxyapatite resin, BioRad Laboratories, Hercules, Calif.), and MEP HYPERCEL™ resin (HCI, hydrophobic charge induction resin, INVITROGEN LIFE TECHNOLOGIES™ Inc., Rockville, Md.) were each packed into 0.66 cm e.d.×20 cm Omni glass columns. The operating conditions for chromatography are presented in Table 1.

TABLE 1

Chromatography Operating Conditions

| Resin | Resin Type | Mode of Operation | Buffers | Load Conditioning |
|---|---|---|---|---|
| SP Sepharose Fast Flow ™ (Amersham Biosciences, Piscataway, NJ) | Cation exchange (S) | Non-specific bind and elute | 20 mM MES, 50 mM NaCl, pH 5.5 10 CV gradient to 500 mM NaCl | <5 mS/cm pH 5.5 |
| Bakerbond ABx ™ (J. T. Baker, Phillipsburg, NJ) | Mixed-mode ion exchange (ABx) | Non-specific bind and elute | Same as S | Same as S |
| Q Sepharose Fast Flow ™ (Amersham Biosciences, NJ) | Anion exchange (Q) | Flow-through | 25 mM Tris, 50 mM NaCl, pH 8 | <7 mS/cm pH 8 |
| Phenyl Sepharose Fast Flow ™, low sub (Amersham Biosciences, NJ) | Hydrophobic interaction (HIC) | Non-specific bind and elute | 50 mM MES, 0.8 M $Na_2SO_4$, pH 6 15 CV gradient to 50 mM MES, pH 6 | 0.8 M $Na_2SO_4$ pH 6 |
| Macro-Prep ceramic hydroxyapatite, Type II (Bio-Rad, Hercules, CA) | Hydroxyapatite (HA) | Non-specific bind and elute | 10 mM sodium phosphate, pH 6.8 10 CV gradient to 400 mM phosphate, pH 6.8 | <3 mS/cm pH 6.8 |
| MEP HYPERCEL ™ (Invitrogen Life Technologies ™, Rockville, MD) | Hydrophobic charge induction (HCI) | Non-specific bind and elute | 25 mM Tris, 50 mM NaCl, 5 mM EDTA, pH 7.1, Step elute with 50 mM acetate, pH 4 | pH > 7 |

All of the columns were loaded to 10 mg antibody per ml resin at a flow rate of 100 cm/h (5 column volumes per hour).

Between uses, S, HIC and HCI resins were sanitized with ≧3 column volumes of 0.5N NaOH. Columns containing ABx, Q, and HA resins were packed with fresh resin before each use.

CHO cells expressing anti-CD11a rhuMAb were cultured and a harvested cell culture formulation containing the antibody was collected. The crude cell culture mixture contained approximately 220,000 ppm CHOP (equivalent to 220,000 ng CHOP/mg anti-CD11a rhuMAb). An aliquot of the crude mixture was applied to each of the resins for Step 1 in Table 2. An aliquot of the eluate from Step 1 was then applied to each of the alternative resins in Step 2 of Table 2, and antibody and impurities were further separated. The buffer conditions for each step are summarized in Table 1. The crude mixture and each eluant pool from the first step were adjusted to the pH and ionic strength of the buffer conditions of the resin to which the crude mixture or eluate pool was applied for the subsequent purification step. A summary of purification results as measured by CHOP concentrations after each of two steps of non-affinity purification is shown in Table 2.

TABLE 2

CHOP removal over two steps of non-affinity purification

| Resin used in Step 1 | CHOP (ppm; ng/mg antibody) | Alternative Resins used in Step 2 | CHOP (ppm; ng/mg antibody) |
|---|---|---|---|
| Test processes: | | | |
| Q | 23,000 | Q | 14,000 |
| | | HIC | 3,000 |
| | | ABx | 1,000 |
| | | S | 900 |
| | | HCI | 11,000 |
| HIC | 26,000 | Q | 9,900 |
| | | HIC | 2,400 |
| | | ABx | 400 |
| | | S | 900 |
| Abx | 6,600 | Q | 3,100 |
| | | HIC | 2,400 |
| | | ABx | 1,700 |
| | | S | 1,000 |
| | | HCI | 2,800 |
| S | 14,000 | Q | 80 |
| | | HIC | 600 |
| | | ABx | 140 |
| | | S | 2,100 |
| Control process: | | | |
| ProA | 300 | S | 30 |

Of the non-affinity steps examined, the ABx column removed the most CHOP impurities from the HCCF, resulting in a CHOP concentration of 6600 ppm. The purity of pools resulting from two steps of non-affinity purification, ranged from 80 ppm to 14,000 ppm CHOP. The purification with S purification as the first step and Q purification as the second step resulted in a low CHOP concentration of 80 ppm. However, when the steps were reversed such that Q purification was the first step and S purification was the second step, the purification yield was a CHOP concentration of 900 ppm. The step order of the non-affinity processes affected the purity results.

Further purification using three steps of non-affinity purification was evaluated and compared to a three step purification process involving one affinity step of Protein A chromatography, i.e. ProA-S-Q, as shown in Tables 3 and 4. As for the studies described above for a 2-step purification process, aliquots of a crude cell culture mixture containing 220,000 ppm CHOP were adjusted for pH and ionic strength according to Table 1 for the resin to which they were applied in Step 1 of Table 3, and similarly for Steps 2 and 3 of Table 3. The results of CHOP removal using processes involving three steps of non-affinity purification are shown in Table 3. The yields of anti-CD11a rhuMAb from some of the three-step non-affinity purification processes are shown in Table 4.

TABLE 3

CHOP removal over three steps of non-affinity purification

| Resin used in Step 1 | [CHOP], ppm, after Step 1 | Resin used in Step 2 | [CHOP], ppm, after Step 2 | Alternative Resins used in Step 3 | [CHOP], ppm, after Step 3 |
|---|---|---|---|---|---|
| Test Processes: | | | | | |
| HIC | 26,000 | ABx | 400 | ABx | 13 |
| | | | | S | 14 |
| | | | | HIC | 20 |
| | | | | Q | 22 |
| S | 14,000 | Q | 80 | ABx | <2 |
| | | | | S | 10 |
| | | | | HIC | <2 |
| | | | | Q | 30 |
| S | 14,000 | ABx | 140 | ABx | 28 |
| | | | | S | 50 |
| | | | | HIC | 6 |
| | | | | Q | <2 |
| Control process: | | | | | |
| ProA | 730 | S | 160 | Q | <2 |

TABLE 4

Yields of anti-CD11a rhuMAb over three steps of non-affinity purification

| Process Steps | | | |
|---|---|---|---|
| Step 1 | Step 2 | Step 3 | Overall Yield |
| Test processes: | | | |
| S 96% | Q 100% | ABx 79% | 76% |
| S 96% | Q 100% | HIC 89% | 85% |
| S 96% | ABx 92% | Q 100% | 88% |
| Control process: | | | |
| ProA 97% | S 89% | Q 98% | 85% |

The combination of two or more steps of non-affinity purification resulted in a purity level, as determined by the elimination of CHOP impurities, of about, for example, 14,000 ppm of CHOP after the first non-affinity step, about 80 ppm of CHOP after the second non-affinity step and about 2 ppm of CHOP after the third step of the process (S-Q-ABx or HIC) (see Table 2), and product purities of anti-CD11a antibody as shown in Table 4.

Example 2

Combination of Non-affinity Chromatography and HPTFF Purification

The present example involves the purification of recombinant human monoclonal antibody, anti-HER2 rhuMAb, with a molecular weight of 160 kD and a pI of about 9.0 from chinese hamster ovary (CHO) cells. The anti-HER2 rhuMAb was obtained from an industrial scale CHO cell culture process at Genentech (South San Francisco, Calif., USA). After CHO cell culture, the anti-HER2 rhuMAb molecule was partially clarified by centrifugation and normal cell filtration to remove cells and cell debris. The resulting pool consisted of 0.52 mg/ml of anti-HER2 rhuMAb product and 0.78 mg/ml of CHOP.

For purification of anti-HER2 rhuMAb, conditioned harvested cell culture fluid (HCCF) comprising an anti-HER2 rhuMAb product and Chinese Hamster Ovary host cell proteins (CHOP) from CHO cells expressing anti-HER2 rhuMAb was loaded onto an initial cation exchange chromatography column (S) (SP-SEPHAROSE FAST FLOW™ Resin, Amersham Biosciences) to remove host cell proteins or CHO proteins (CHOP), variants, and aggregates. Elutions from the S column were pooled (S pool) and subjected to a second anion exchange chromatography column (Q) (Q-SEPHAROSE FAST FLOW™ resin, Amersham Biosciences, Piscataway, N.J.) to remove CHOP and target protein aggregates. The flow-through from the Q column (Q pool) was subdivided and each pool was further subjected to a third process of HPTFF for further removal of CHOP, variants and small molecules. Two of the Q pools were subjected to HPTFF Experiment 1 and HPTFF Experiment 2 as described in detail below.

A. Non-affinity Chromatography

The chromatography columns were loaded to approximately 10 grams of rhuMAb/liter of resin for a total of about 40 grams of rhuMAb at a flow rate of 100 cm/h (5 column volumes (CVs) per hour).

1. Methods

For preparation of the non-affinity chromatography columns, bind-and-elute SP-Sepharose and flow-through Q-Sepharose were each packed into preparative scale columns. The operating conditions for each chromatography column are presented in Table 5.

TABLE 5

Non-affinity Chromatography Operating Conditions

| Resin | Resin Type | Mode of Operation | Buffers | Load Conditioning |
|---|---|---|---|---|
| SP Sepharose Fast Flow ™ (Amersham Biosciences, Piscataway, NJ) | Cation exchange (S) | Non-specific bind and elute | 25 mM MES, 20 mM NaCl, pH 5.5 10 CV gradient to 500 mM NaCl | <6 mS/cm pH 5.5 |
| Q Sepharose Fast Flow ™ (Amersham Biosciences, NJ) | Anion exchange (Q) | Flow-through | 25 mM Tris, 50 mM NaCl, pH 8 | <8 mS/cm pH 8 |

The HCCF was conditioned by diluting the HCCF to a conductivity of less than 6 mS/cm with water and adjusting the HCCF to a pH of 5.5 with HCl and filtered through a 0.22 μm filter. A volume of 66 liters of conditioned HCCF was subjected to non-affinity chromatography.

The SP-Sepharose column was equilibrated with 5 column volumes (CVs) of the column buffer (Table 5). The 66 liters of conditioned HCCF (<10 g/l) were loaded onto the equilibrated SP-Sepharose column. After loading the conditioned HCCF onto the SP-Sepharose column, the column was washed with 5 CVs of column buffer. Elutions were made with elution buffer (25 mM MES, 500 mM NaCl, pH 5.5) with eluant collected at an absorbance of from 0.1-0.2 AU at 280 nm. The chromatography resin was regenerated in a 0.5 M NaOH solution and further stored in 0.1 M NaOH.

The collections from the SP-Sepharose column were pooled (SP pool) and conditioned by diluting the S pool to a conductivity of approximately 7.5 to 8 mS/cm with water and adjusted to a pH of 8 with NaOH. The conditioned S pool was then filtered through a 0.22 μm filter. The filtered SP pool (about 9 liters) was loaded onto a Q-Sepharose column that was equilibrated with 5 CVs of the column buffer (see Table 5). The flow-through was collected at 0.2-0.2 AU at 280 nm and the flow-through was pooled (Q pool). A total of 20.6 liters of the Q pool was collected.

The Q-Sepharose chromatography resin was regenerated in a 0.5 M NaOH solution and further stored in 0.1 M NaOH. The 20.6 liters recovered from the Q column was divided into 3 identical pools, each having a volume of 6.9 liters and a concentration of about 1.4 g/L of anti-HER2 rhuMAb, prior to HPTFF purification.

2. Analysis

The amount of anti-HER2 rhuMAb in each pool following a purification step of the process, i.e. in the HCCF and in the pools from the purification process, was determined by an HPLC analysis based on Protein-A immunoaffinity. The HPLC column was a Poros Protein A, 4.6 mm i.d.×100 mm bed height (PerSeptive Biosystems). Samples and standards were applied to the column in a loading buffer, the rhuMAb analyte bound to the column, then was eluted under acidic conditions. The peak area of the eluted material was compared to the peak area of a standard curve to calculate the amount of rhuMAb. The assay range was typically 0.05 mg/mL to 1.0 mg/mL.

Upon completion of the S and Q chromatography, samples from pools. were subjected to SDS-PAGE analysis (FIG. 2, lanes 4 and 5, respectively). Samples were analyzed by sodium dodecyl sulfate polyacrylamide gel electrophoresis (SDS-PAGE), which separated proteins according to size (relative hydrodynamic radius). Samples and the molecular weight standard (ranging from 10 to 200 kDa) were prepared under non-reducing conditions and loaded onto a gel at approximately 2.5 µg/lane. A 10% to 20% acrylamide gradient gel, 8 cm×8 cm size, was used herein (Zaxis International, Inc., Hudson, Ohio) and was electrophoresed at a constant voltage of 170 mV. Following the electrophoresis, the proteins were stained to be rendered visible. The electrophoresed gel was then treated by silver staining according to the method described by Morrisey (Morrisey, J., Analytical Biochemistry, 1981, 117: 307-310). The results are shown in FIG. 2.

To determine the amount of anti-HER2 rhuMAb present in each pool as the intact monomer, the mixtures were subjected to Size Exclusion Chromatography (SEC) according to the following procedure. Briefly, a Superdex 200 HR 10/30 column (Amersham Biosciences, Piscataway, N.J.) was equilibrated in phosphate buffer saline Approximately 100 µg of rhuMAb per sample was applied to the column. The sample was eluted from the column based on the molecular size of the protein molecules contained in the sample (optimal separation range: 10 to 600 kDa). The absorbance of the column eluate was measured at 280 nm and the protein elution peaks were integrated to determine the percent area of monomeric rhuMAb. The percentages of intact monomer anti-HER2 rhuMAb in the HCCF, S pool, Q pool, and HPTFF pool are shown in Table 8.

CHOP concentration was determined by an enzyme-linked immunosorbent (ELISA) assay using goat anti-(host-cell protein) antibodies to quantify CHOP. Affinity-purified goat whole anti-CHOP antibodies were immobilized on microtiter plate wells. Dilutions of the pool samples, containing CHOP, were incubated in the wells, followed by incubation with conjugated-peroxidase whole anti-CHOP. The horseradish peroxidase was then quantified with o-phenylenediamine by reading the absorbance at 492 nm. Based on the principle of sandwich ELISA, the concentration of peroxidase corresponded to the CHOP concentration. The assay range for the ELISA was typically 5 ng/mL to 320 ng/mL. Depending on the concentration of the samples, 2 to 4 dilutions per sample were assayed and the dilution-corrected results were averaged.

B. HPTFF

High Performance Tangential Flow Filtration (HPTFF) is a two-dimensional filtration operation that involves separation of solutes with less than a 10-fold size difference based on both size and charge. As mentioned above, the Q pool was divided into three equivalent Q pools, each with a volume of 6.9L and a concentration of about 1.4 g/L of anti-HER2 rhuMAb, prior to further purification by HPTFF. Two of the Q pools were subjected to HPTFF Experiment 1, each involving different conditions. Upon determination of the optimum conditions for HPTFF from the HPTFF Experiment 1 studies, combined pools from HPTFF Experiments 1 and 2 were subjected to additional HPTFF as described in detail below.

1. Membrane

Filtration membranes used for HPTFF in these Examples are Composite Regenerated Cellulose (CRC)-Millipore ULTRACEL™ (Millipore) with a nominal molecular weight cut-off of 300 kD (PLCMK). CRC300 mini-PELLICON2® membranes (Millipore) was charge-modified as described herein, resulting in the charged cellulose membrane CRC300+ used in the HPTFF studies of this Example. Briefly, a 300 kD PELLICON-2® cassette (membrane area of 0.1 m$^2$) was used for the scale-down experiment (minimum of 1L solution). The membrane was cleaned according to a cartridge preparation protocol before the first use to remove any residual storage and shipping solution and to equilibrate the membrane to the appropriate buffer condition. The membrane was chemically modified in situ using bromo-propyl-trimethyl-ammonium bromide (Sigma-Aldrich, St Louis, Mo.) under alkaline conditions (PCT/US00/19964, the entire contents of which is hereby incorporated by reference). Specifically, the membrane was charged without co-current filtrate flow, at constant filtrate flux of 100 $lm^{-2}h^{-1}$, retentate pressure fixed at 10 psig, total recycle with filtrate open mode with 1L of ligand dissolved in 0.1N NaOH and 0.2 µm filtered. The Lp before charging was about 53 $lm^{-2}h^{-1}$/psi in 0.1N NaOH, and the Lp after charging was about 37 $lm^{-2}h^{-1}$/psi in 0.1N NaOH. After charging, the resulting positively charged membrane was cleaned using 0.1N sodium hydroxide, sanitized with 300 ppm of MINNCARE™ solution, and stored in 0.1N sodium hydroxide. Before each HPTFF experiment, the membrane was flushed with the first diafiltration buffer of the experiment to remove storage solution and was tested for integrity. Membrane permeability was measured using the HPTFF system with co-current filtrate flow at a minimum of three filtrate fluxes.

2. HPTFF Filtration System

HPTFF experiments were performed using a fully automated tangential flow filtration system with the basic configuration illustrated in FIG. 1. The HPTFF system included a 40-liter stainless steel recycle tank, feed and filtrate flow meters (Admag Model 102 and 105, Johnson Yokogawa Corp., Newman, Ga.) and pressure transducers (Model MSP220-A2, 0-100 psig=0-7 bar, Anderson Instruments, Fultonville, N.Y.). The feed and co-current filtrate flow pumps were positive displacement pumps (Universal 6, Waukesha-Cherry Burrell, Delavan, Wis.) while the diafiltration and filtrate pumps were peristaltic pumps (Model L-7518-62, Cole Parmer, Niles, Ill.). The recycle tank included a temperature probe (Model RIX, −29° C. to 82° C., Moore Industries, Sepulveda, Calif.). All piping was constructed of 316L stainless steel. The retentate pressure control valve was actuated using a steel diaphragm (Model ½ Mikroseal packless control valve, H. D. Baumann, Portsmouth, N.H.), while all other valves were pneumatically actuated with ethylene propylene diene monomer diaphragms (Biotek Model 8836-18-BH, ITT Sherotec, Simi Valley, Calif.). Continuous tank liquid level was measured with a magneto restrictive probe (Model Tempsonics II, MTS, Research Triangle Park, N.C.). Data acquisition and control were performed using proprietary software (Genentech, Inc., South San Francisco, Calif.) using a MycroAdvantage software shell (Moore Products, Springhouse, Pa.).

HPTFF was conducted at a fixed feed flow rate of 323 $l.m^{-2}.h^{-1}$ (volumetric feed flow rate divided by the membrane area) and a retentate pressure of 10 psi. The co-current filtrate flow rate was controlled to reach equal transmembrane pressure at the inlet (feed) and outlet (retentate) of the membrane cassette. The filtrate flux was set at 50 $l.m^{-2}.h^{-1}$ by adjusting the filtrate pump rate. The start-up of HPTFF experiments included a ramp-up of all flow rates in order to minimize the difference between transmembrane pressure at the inlet and outlet of the cassette. The retentate was recycled to the feed tank, while the filtrate was directed to a collection vessel. Feed and filtrate samples were collected in both cases for product and HCP analysis.

a. HPTFF Experiment 1

After the division of the Q pool, as described above, into equivalent 6.9L Q pools, one of the Q pools was subjected to HPTFF Experiment 1 using a CRC300+ membrane under the following conditions.

The charged membranes were equilibrated in the first diafiltration buffer for this experiment (see Table 7). The Q pool was diluted to lower the ionic strength and conductivity of the rhuMAb pool to 2.7 mS/cm, adjusted to a pH of 4.5 and then added to the feed tank (FIG. 1). The material in the feed tank was subjected to concentration by removal of a portion of the solution. When the bulk volume reached a bulk concentration ($C_b$) of 10 g/L, the solution in the feed tank was subjected to sequential diafiltration steps. With a constant conductivity of 1.5 mS/cm, diafiltration was performed with 10 diavolumes at a pH of 4.5 and 5 diavolumes each of pH 5.0, pH 5.5, pH 6.0, and pH 6.5 (Table 7). The yield was calculated based on the quantifiable product sieving during diafiltration using the following equation: $Y=e^{-NS_{Targetprotein}}$ where S is the sieving of the target protein and N the number of diavolumes.

The product quality of the recovered pool from the HPTFF Experiment 1 was subjected to analysis, including SDS-PAGE gel electrophoresis (FIG. 2, lanes 10), rhuMAb % intact monomer analysis and CHOP concentration analysis (Table 8), as described above.

Significant sieving of CHOP was observed with CRC300+ without any significant loss of anti-HER2 rhuMAb. The final concentration of CHOP in the recovered pool from HPTFF performed with CRC300+ was 21 ppm.

b. HPTFF Experiment 2

Another of the Q pools, as described above, having 1.4 mg/ml of rhuMAb, 410 ppm of CHOP, a pH of 5.6 and a conductivity of about 8 mS/cm, was subjected to a HPTFF Experiment 2.

As described above, the CRC300+ membrane was equilibrated in the first diafiltration buffer for this HPTFF Experiment 2 (see Table 7). The Q pool was diluted with water to lower the conductivity to 2.4 mS/cm. The pH was adjusted to pH 4.5 with HCl. The resulting conditioned pool was loaded onto the feed tank. In a single operation, the conditioned pool was then concentrated to 10 g/L at pH 4.5, followed by a constant retentate volume diafiltration comprising a specific sequence of diafiltration buffers (Table 7). Three sequences of diafiltration buffers were selected as follows: 10 diavolumes each at a pH of 4.5, 5.5, and 6.5, at a constant conductivity of 1.5 mS/cm. All HPTFF experiments were conducted at a filtrate flux of 50 $l.m^{-2}.h^{-1}$ using a positively charged Pellicon-2® mini cassette with a permeability of 36 $l.m^{-2}.h^{-1}/psi$.

Upon completion of the HPTFF process performed with CRC300+, a sample of the recovered pool was subjected to SDS-PAGE analysis (FIG. 2, lane 11). The product quality of the recovered pool from the HPTFF Experiment 2 was subjected to additional analysis, including Size Exclusion Chromatography (SEC) and CHOP concentration analysis (Table 8).

The purification factors for the HPTFF step was greater than 24 (i.e. 24-fold removal of CHOP) and CHOP removal occurred during both concentration and diafiltration. The

TABLE 7

Experimental conditions and results from HPTFF step of purification

| | Concentration $C_b$ (g/L) | Diafiltration pH-N | Yield (%) | [CHOP]$_{final}$ ppm |
|---|---|---|---|---|
| Q pool | | | | 410 |
| HPTFF Experiment 1 | 10 | 4.5-10 | 99% | 21 |
| | | 5.0-5 | | |
| | | 5.5-5 | | |
| | | 6.0-5 | | |
| | | 6.5-5 | | |
| HPTFF Experiment 2 | 10 | 4.5-10 | 99% | 17 |
| | | 5.5-10 | | |
| | | 6.5-10 | | |
| Additional HPTFF (Combined pools from HPTFF 1 & 2) | 10 | 6.5-40 | 99% | 2.2 |
| | | 6.0-5 | | |

CHOP concentration was reduced from 410 ppm (concentration in the material recovered from the Q chromatography column) to 17 ppm (concentration in the material recovered from the HPTFF Experiment 2) (see Table 8). No significant filtrate losses were observed.

TABLE 8

CHO host cell protein quantification and purity analysis of anti-HER2 rhuMAb feedstream in purification processes

| Purification Step | [CHOP] (ppm) | % intact rhuMAb monomer (measured by SEC) |
|---|---|---|
| HCCF | 1,469,000 | — |
| S pool | 144,780 | 95.9% |
| Q pool | 410 | 97.4% |
| HPTFF Experiments 1, 2 | 21, 17 | 99.8% |
| Control Process: (using steps:ProA-S-Q-UFDF) | <1 | 100% | c. Additional HPTFF

Material recovered after the HPTFF Experiments 1 and 2 was combined and further subjected to additional HPTFF as follows.

As described above, the CRC300+ membrane was equilibrated in the first diafiltration buffer and the combined material was loaded onto the feed tank. The material in the feed tank was subjected to optimal sequential diafiltration steps as follows: 40 diavolumes at pH 6.5 and 1.5 mS/cm, followed by 5 diavolumes at pH 6.0 and 0.3 mS/cm.

The additional HPTFF process reduced the concentration of CHOP in the final retentate to 2.2 ppm. A sample of the recovered material after the additional was subjected to SDS-PAGE analysis. The product quality of the material recovered after additional HPTFF (FIG. 2, lanes 6 and 12) as determined by SDS-PAGE analysis was compared to the product quality of material obtained through a conventional purification process involving ProA, SP, Q and UFDF (FIG. 2, lane 7).

The purification process, involving two steps of non-affinity purification and a third step of HPTFF, resulted in a purity level, as determined by the elimination of CHOP impurities, of about 144,780 ppm of CHOP after S purification, of about 410 ppm CHOP after Q purification, and a final purity of about 17-21 ppm of CHOP. Further purity of about 2.2 ppm of CHOP was achieved by additional HPTFF, which further purification is alternatively incorporated into the third step, thereby providing a three-step non-affinity process comparable to traditional methods using costly affinity chromatography.

Example 3

Combination of Non-affinity Chromatography and HPTFF Purification

The present example involves the purification of recombinant human monoclonal antibody, anti-CD40 rhuMAb, with a molecular weight of 160 kD and a pI of about 9.3 from chinese hamster ovary (CHO) cells. The anti-CD40 rhuMAb was obtained from an industrial scale CHO cell culture process at Genentech (South San Francisco, Calif., USA). After CHO cell culture, the anti-CD40 rhuMAb molecule was partially clarified by centrifugation and normal cell filtration to remove cells and cell debris. The resulting pool consisted of 1.7 mg/ml of anti-CD40 rhuMAb product and approximately 0.4 mg/ml of CHOP.

For purification of anti-CD40 rhuMAb, conditioned harvested cell culture fluid (HCCF) comprising an anti-CD40 rhuMAb product and Chinese Hamster Ovary host cell proteins (CHOP) from CHO cells expressing anti-CD40 rhuMAb was loaded onto an initial cation exchange chromatography column (S) (SP-SEPHAROSE FAST FLOW™ Resin, Amersham Biosciences) to remove host cell proteins or CHO proteins (CHOP), variants, DNA impurities and aggregates. Elutions from the S column were pooled (S pool) and subjected to a second anion exchange chromatography column (Q) (Q- SEPHAROSE FAST FLOW™ resin, Amersham Biosciences, Piscataway, N.J.) to remove CHOP, DNA impurities and target protein aggregates. The flow-through from the Q column (Q pool) was further subjected to a third process of HPTFF for further removal of CHOP, variants and small molecules.

A. Non-affinity Chromatography

1. Methods

For preparation of the non-affinity chromatography columns, bind-and-elute SP-Sepharose and flow-through Q-Sepharose were each packed into preparative scale columns. The operating conditions for each chromatography column are presented in Table 9.

TABLE 9

Non-affinity Chromatography Operating Conditions

| Resin | Resin Type | Mode of Operation | Column Buffers | Load Conditioning |
|---|---|---|---|---|
| SP Sepharose Fast Flow ™ (Amersham Biosciences, Piscataway, NJ) | Cation exchange (S) | Non-specific bind and elute | 20 mM MES, 50 mM NaAcetate, pH 6.5 | <7.0 mS/cm pH 6.5 |
| Q Sepharose Fast Flow ™ (Amersham Biosciences, NJ) | Anion exchange (Q) | Flow-through | 25 mM Tris, 50 mM NaCl, pH 8 | <8 mS/cm pH 8 |

The HCCF was conditioned by diluting the HCCF to a conductivity of less than 7 mS/cm with water and adjusting the HCCF to a pH of 6.5 with acetic acid and filtered through a 0.22 μm filter. The SP-Sepharose column was equilibrated with 4 column volumes (CVs) of the column buffer (Table 9) and loaded to approximately 30 grams of rhuMAb/liter of resin for a total of about 13 grams of rhuMAb at a flow rate of 150 cm/h. After loading the conditioned HCCF onto the SP-Sepharose column, the column was washed with 5 CVs of wash buffer (20 mM HEPES, 35 mM NaAcetate, pH 8.0) followed by 3 CVs of column buffer (Table 9). Elutions were made with a 10 CV gradient elution from the column buffer to the elution buffer 20 mM MES, 140 mM NaAcetate, pH 6.5, with the eluant collected at an absorbance of from 0.1 to 0.5 AU at 280 nm. The chromatography resin was regenerated in a 0.5 M NaOH solution and further stored in 0.1 M NaOH.

The SP-Sepharose pool (SP pool) was conditioned by diluting the S pool to a conductivity of approximately 7.5 mS/cm with water and adjusted to a pH of 8 with NaOH. The conditioned S pool, having a total mass of about 9 grams, was then filtered through a 0.22 μm filter. The filtered conditioned SP pool was loaded onto a Q-Sepharose column that was equilibrated with 5 CVs of the column buffer (see Table 9). The flow-through was collected at 0.2-0.2 AU at 280 nm and the flow-through was pooled (Q pool). The Q-Sepharose chromatography resin was regenerated in a 0.5 M NaOH solution and further stored in 0.1 M NaOH.

2. Analysis

The amount of anti-CD40 rhuMAb in each pool following a purification step of the process, i.e. in the HCCF and in the pools from the purification process, was determined by an HPLC analysis based on Protein-A immunoaffinity as described in the Example 2 herein. CHOP concentration was determined using the enzyme-linked immunosorbent (ELISA) assay described in the Example 2 herein. Upon completion of the S and Q chromatography, samples from pools were subjected to SDS-PAGE analysis (FIG. 5, lanes 3 and 4, respectively). The Q pool was diluted to lower the ionic strength and conductivity of the rhuMAb pool to 1.8 mS/cm, adjusted to a pH of 4.5 and then added to the recycle tank (FIG. 1). The HPTFF experiment purification step using a positively charged CRC300+ membrane (the HPTFF experiment) was begun by first concentrating the material from the Q pool until the bulk volume reached a bulk concentration ($C_b$) of 10 g/L. The resultant solution in the recycle tank was then subjected to sequential diafiltration steps. With a constant conductivity of 1.5 mS/cm, diafiltration was performed with 5 diavolumes each at a pH 4.5 and pH 5.5, followed by 20 diavolumes at pH 6.5, followed by 10 diavolumes at pH 7.0 (Table 10). The yield was calculated based on the quantifiable product sieving during diafiltration using the following equation: $Y = e^{-NS_{Targetprotein}}$ where S is the sieving of the target protein and N the number of diavolumes.

TABLE 10

Experimental conditions and results from HPTFF step of purification

| | Concentration $C_b$ (g/L) | Diafiltration pH - N | Yield (%) | [CHOP] (ppm) | [DNA] (ppm) |
|---|---|---|---|---|---|
| Q pool | | | 96% | 15 | 15 |
| HPTFF pool | 10 | 4.5-5 5.5-5 6.5-20 7.0-10 | 99% | <0.6 | <0.6 |

The product quality of the recovered pool from this HPTFF experiment was subjected to analysis including SDS-PAGE gel electrophoresis (FIG. 5, lane 5), rhuMAb % intact monomer analysis, and CHOP concentration analysis (Table 11), as described in Example 2, herein. DNA concentration was evaluated according to the THRESHOLD® Total DNA Assay (Molecular Devices, Corp., Sunnyvale, Calif.) (Table 11). The THRESHOLD® Total DNA Assay is specific for single-stranded DNA, which is obtained from the sample via denaturation by heat. The single-stranded DNA is labeled with binding proteins, which are covalently bound to urease and streptavidin, and form a DNA complex. The DNA complex is filtered through a biotin coated nitrocellulose membrane known as a "stick." The biotin on the membrane reacts with streptavidin in the DNA complex, capturing the complex. The stick is placed in the Threshold Reader, which contains the substrate, urea. The enzymatic reaction between urea and urease (in the DNA complex) changes the local pH of the substrate solution. A silicon sensor records a change in surface potential, which is proportional to the pH change. The rate of change in surface potential is proportional to the amount of DNA. Quantification of samples is determined by comparison to DNA standards. Samples were diluted so that the DNA content falls within the reporting range of the standard curve (10-400 pg/mL).

Significant sieving of CHOP was observed with positively charged CRC300+ HPTFF membrane without any significant loss of positively charged anti-CD40 rhuMAb. CHOP removal occurred during both concentration and diafiltration. The CHOP concentration was reduced from 15 ppm (concentration in the material recovered from the Q chromatography column) to less than 0.6 ppm within the first 20 diavolumes (concentration in the protein pool in the recycle tank). The removal of CHOP impurities was confirmed by measuring the concentration in the material recovered from the HPTFF experiment (see Table 11). No significant filtrate losses were observed.

TABLE 11

CHO host cell protein quantification and purity analysis of anti-CD40 rhuMAb feedstream in purification processes

| Purification Step | [CHOP] (ppm) | % intact rhuMAb monomer (measured by SEC) | [DNA] (ppm) |
|---|---|---|---|
| HCCF | 240,000 | — | >5441 |
| S pool | 530 | — | 0.1 |
| Q pool | 15 | — | <0.01 |
| HPTFF pool | <0.6 | 99.5% | <0.006 |
| Control Process: (using steps: ProA-S-Q-UFDF) | 3 | 99.5% | <0.003 |

The purification process, involving two steps of non-affinity purification and a third step of HPTFF, resulted in a purity level, as determined by (1) the elimination of CHOP impurities, of about 530 ppm of CHOP after S purification, of about 15 ppm CHOP after Q purification, and a final purity of about less than 0.6 ppm of CHOP within 20 diavolumes, and by (2) the elimination of DNA impurities, of about 0.1 ppm of CHOP after S purification, of about less than 0.01 ppm DNA after Q purification, and a final purity of about less than 0.006 ppm of DNA. In addition, the electrophoresis analysis illustrated the comparable purity of the non-affinity final pool (FIG. 5, lane 5) to that a conventional pool obtained using an affinity step (FIG. 5, lane 10).

FIG. 5 shows a silver-stained SDS-PAGE gel containing samples that were taken at different points during the purification of anti-CD40 recombinant human monoclonal antibody (rhuMAb) according to Example 3 (lanes 2-5) and compared to a conventional purification process including an affinity purification step (lanes 8-10). The arrows indicating 160 kD, 50 kD, and 25 kD point to the full length antibody, the heavy chain, and the light chain, respectively. Other bands are anti-CD40 rhuMAb fragments. Lane 1 is a mixture of protein standards. Lanes 2-6 are samples taken after performance of the non-affinity process disclosed in Example 3 herein in which host cell culture fluid (HCCF) (lane 2) was purified by cation exchange chromatography (S pool, lane 3), followed by an anion exchange chromatography (Q pool, lane 4), followed by HPTFF using a charged membrane (HPTFF pool, lane 5), followed by and compared to material recovered after rinsing the HPTFF membrane and the feed side of the HPTFF apparatus (HPTFF buffer flush pool, lane 6). Lane 7 is blank. Lanes 8-10 correspond to anti-CD40 in an HCCF mixture purified by a conventional recovery process including a protein A affinity chromatography step (not shown), followed by a cation exchange chromatography step (lane 8), followed by an anion exchange chromatography (lane 9), and followed by an ultrafiltration step (lane 10).

This purification scheme provided a three-step non-affinity process comparable to traditional methods using costly affinity chromatography.

The foregoing written specification is considered to be sufficient to enable one skilled in the art to practice the invention. The present invention is not to be limited in scope by the examples presented herein, since the exemplified embodiments are intended as illustrations of certain aspects of the invention and any functionally equivalent embodiments are within the scope of this invention. The examples presented herein are not intended as limiting the scope of the claims to the specific illustrations. Indeed, various modifications of the invention, in addition to those shown and described herein and which fall within the scope of the appended claims, may become apparent to those skilled in the art from the foregoing description.

---

What is claimed is:

1. A method for purifying a target protein from a mixture containing a host cell protein, consisting essentially of subjecting said mixture to:
    (a) a first non-affinity purification step, and
    (b) a second non-affinity purification step, followed by
    (c) high-performance tangential-flow filtration (HPTFF), and
    (d) isolating said protein in a purity containing less than 100 parts per million (ppm) of said host cell protein, wherein said method includes no affinity purification step.

2. The method of claim 1 wherein said first and second non-affinity purification steps are different and are selected from the group consisting of ion exchange chromatography and hydrophobic interaction chromatography.

3. The method of claim 2 wherein said ion exchange chromatography is selected from the group consisting of cation exchange chromatography, anion exchange chromatography and mixed mode ion exchange chromatography.

4. The method of claim 3 wherein said first and second affinity purification steps are cation exchange chromatography and anion exchange chromatography, in either order.

5. The method of claim 3 wherein said first non-affinity purification step is cation exchange chromatography and said second non-affinity purification step is anion exchange chromatography.

6. The method of claim 5 wherein said method consists of purification steps (a)-(c) followed by isolation step (d).

7. The method of claim 5 wherein said cation exchange chromatography step is performed on a cation exchange resin selected from the group consisting of a carboxy-methyl cellulose resin, a mixed mode ion exchange resin, sulphopropyl immobilized on agarose, and sulphonyl immobilized on agarose.

8. The method of claim 5 wherein said anion exchange ligand is selected from the group consisting of diethylaminoethyl (DEAE) and quaternary ammonium ions.

9. The method of claim 1 wherein the HPTFF is performed using a charged membrane.

10. The method of claim 1 wherein said host cell protein is Chinese Hamster Ovary Protein (CHOP).

11. The method of claim 1 wherein said target protein is an antibody.

12. The method of claim 11 wherein said antibody is a monoclonal antibody.

13. The method of claim 11 wherein said antibody is a polyclonal antibody.

14. The method of claim 11 wherein said antibody is a humanized antibody.

15. The method of claim 11 wherein said antibody is a human antibody.

16. The method of claim 11 wherein said antibody is an antibody fragment.

17. The method of claim 11 wherein said antibody fragment is selected from the group consisting of Fab, Fab', F(ab')$_2$ and Fv fragments, single-chain antibody molecules, diabodies, linear antibodies, bispecific antibodies and multispecific antibodies formed from antibody fragments.

18. The method of claim 11 wherein said antibody specifically binds to an antigen selected from the group consisting of CD3, CD4, CD8, CD19, CD20, CD34, CD40, EGF receptor, HER2, HER3, HER4 receptor, LFA-1, Mac1, p150,95, VLA-4, ICAM-1, VCAM, av/b3 integrin, CD11a, CD18, CD11b, VEGF, IgE, flk2/flt3 receptor, obesity (OB) receptor, mpl receptor, CTLA-4, and polypeptide C.

19. The method of claim 11 wherein said antibody is selected from the group consisting of anti-HER2; anti-CD20; anti-IL-8; anti-VEGF; anti-PSCA; anti-CD11a; anti-IgE; anti-Apo-2 receptor; anti-TNF-ÿ; anti-Tissue Factor (TF); anti-CD3; anti-CD25; anti-CD34; anti-CD40; anti-tac; anti-CD4; anti-CD52; anti-Fc receptor; anti-carcinoembryonic antigen (CEA)antibodies; antibodies directed against breast epithelial cells; antibodies that bind to colon carcinoma cells; anti-CD33; anti-CD22; anti-EpCAM; anti-GpIIb/IIIa; anti-RSV; anti-CMV; anti-HIV; anti-hepatitis; anti-ÿvÿ; anti-human renal cell carcinoma; anti-human 17-1A; anti-human colorectal tumor; anti-human melanoma; anti-human squamous-cell carcinoma; and anti-human leukocyte antigen (HLA) antibodies.

20. The method of claim 11 wherein said antibody is selected from the group consisting of anti-HER2 receptor, anti-VEGF, anti-IgE, anti-CD20, anti-CD 11a, and anti-CD40 antibodies.

21. The method of claim 1 wherein the target protein is an immunoadhesin.

22. The method of claim 1 wherein the target protein is an antibody-like molecule.

23. The method of claim 22 wherein said antibody-like molecule is a protein fused to, or conjugated with, a $C_H2/C_H3$ region.

24. The method of claim 23 wherein said protein is selected from the group consisting of renin; growth hormones; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; factor VIIIC; factor IX; tissue factor; von Willebrands factor; Protein C; atrial natriuretic factor; lung surfactant; urokinase; human urine and tissue-type plasminogen activator (t-PA); bombesin; thrombin; hemopoietic growth factor; tumor necrosis factor-alpha and -beta; enkephalinase; RANTES; human macrophage inflammatory protein (MIP-1-alpha); serum albumins; Muellerian-inhibiting substance; relaxin A-chain; relaxin B-chain; prorelaxin; mouse gonadotropin-associated peptide; beta-lactamase; DNase; IgE; cytotoxic T-lymphocyte associated antigens (CTLAs); inhibin; activin; vascular endothelial growth factor (VEGF); receptors for hormones or growth factors; Protein A or D; rheumatoid factors; bone-derived neurotrophic factor (BDNF); neurotrophin-3, -4, -5, and -6 (NT-3, NT-4, NT-5, and NT-6), nerve growth factors; platelet-derived growth factor (PDGF); fibroblast growth factors; epidermal growth factor (EGF); transforming growth factors (TGF); insulin-like growth factor-I and -II (IGF-I and IGF-II; des(1-3)-IGF-I (brain IGF-I), insulin-like growth factor binding proteins (IGFBPs); CD proteins; erythropoietin; osteoinductive factors; immunotoxins; bone morphogenetic proteins (BMPs); interferons-alpha, -beta, and -gamma; colony stimulating factors (CSFs); interleukins IL-1 to IL-10; superoxide dismutase; T-cell receptors; surface membrane proteins; decay accelerating factor; viral antigens; transport proteins; homing receptors; addressins; regulatory proteins; integrins; tumor associated antigens; and fragments and thereof.

25. The method of claim 1, further comprising the step of incorporating the isolated protein into a pharmaceutical formulation.

* * * * *

SEQUENCE LISTING

```
<160> NUMBER OF SEQ ID NOS: 4

<210> SEQ ID NO 1
<211> LENGTH: 214
<212> TYPE: PRT
<213> ORGANISM: Artificial Sequence
<220> FEATURE:
<223> OTHER INFORMATION: Sequence is synthesized

<400> SEQUENCE: 1

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Val Asn
                20                  25                  30

Thr Ala Val Ala Trp Tyr Gln Gln Lys Pro Gly Lys Ala Pro Lys
                35                  40                  45

Leu Leu Ile Tyr Ser Ala Ser Phe Leu Tyr Ser Gly Val Pro Ser
                50                  55                  60

Arg Phe Ser Gly Ser Arg Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

His Tyr Thr Thr Pro Pro Thr Phe Gly Gln Gly Thr Lys Val Glu
                95                  100                 105

Ile Lys Arg Thr Val Ala Ala Pro Ser Val Phe Ile Phe Pro Pro
                110                 115                 120

Ser Asp Glu Gln Leu Lys Ser Gly Thr Ala Ser Val Val Cys Leu
                125                 130                 135

Leu Asn Asn Phe Tyr Pro Arg Glu Ala Lys Val Gln Trp Lys Val
                140                 145                 150

Asp Asn Ala Leu Gln Ser Gly Asn Ser Gln Glu Ser Val Thr Glu
                155                 160                 165

Gln Asp Ser Lys Asp Ser Thr Tyr Ser Leu Ser Ser Thr Leu Thr
                170                 175                 180

Leu Ser Lys Ala Asp Tyr Glu Lys His Lys Val Tyr Ala Cys Glu
                185                 190                 195
```

```
Val Thr His Gln Gly Leu Ser Ser Pro Val Thr Lys Ser Phe Asn
                200                 205                 210

Arg Gly Glu Cys
```

<210> SEQ ID NO 2
<211> LENGTH: 449
<212> TYPE: PRT
<213> ORGANISM: Artificial Sequence
<220> FEATURE:
<223> OTHER INFORMATION: Sequence is synthesized

<400> SEQUENCE: 2

```
Glu Val Gln Leu Val Glu Ser Gly Gly Gly Leu Val Gln Pro Gly
  1               5                  10                  15

Gly Ser Leu Arg Leu Ser Cys Ala Ala Ser Gly Phe Asn Ile Lys
                 20                  25                  30

Asp Thr Tyr Ile His Trp Val Arg Gln Ala Pro Gly Lys Gly Leu
                 35                  40                  45

Glu Trp Val Ala Arg Ile Tyr Pro Thr Asn Gly Tyr Thr Arg Tyr
                 50                  55                  60

Ala Asp Ser Val Lys Gly Arg Phe Thr Ile Ser Ala Asp Thr Ser
                 65                  70                  75

Lys Asn Thr Ala Tyr Leu Gln Met Asn Ser Leu Arg Ala Glu Asp
                 80                  85                  90

Thr Ala Val Tyr Tyr Cys Ser Arg Trp Gly Gly Asp Gly Phe Tyr
                 95                 100                 105

Ala Met Asp Tyr Trp Gly Gln Gly Thr Leu Val Thr Val Ser Ser
                110                 115                 120

Ala Ser Thr Lys Gly Pro Ser Val Phe Pro Leu Ala Pro Ser Ser
                125                 130                 135

Lys Ser Thr Ser Gly Gly Thr Ala Ala Leu Gly Cys Leu Val Lys
                140                 145                 150

Asp Tyr Phe Pro Glu Pro Val Thr Val Ser Trp Asn Ser Gly Ala
                155                 160                 165

Leu Thr Ser Gly Val His Thr Phe Pro Ala Val Leu Gln Ser Ser
                170                 175                 180

Gly Leu Tyr Ser Leu Ser Ser Val Val Thr Val Pro Ser Ser Ser
                185                 190                 195

Leu Gly Thr Gln Thr Tyr Ile Cys Asn Val Asn His Lys Pro Ser
                200                 205                 210

Asn Thr Lys Val Asp Lys Lys Val Glu Pro Lys Ser Cys Asp Lys
                215                 220                 225

Thr His Thr Cys Pro Pro Cys Pro Ala Pro Glu Leu Leu Gly Gly
                230                 235                 240

Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val
                275                 280                 285

Glu Val His Asn Ala Lys Thr Lys Pro Arg Glu Glu Gln Tyr Asn
                290                 295                 300

Ser Thr Tyr Arg Val Val Ser Val Leu Thr Val Leu His Gln Asp
                305                 310                 315
```

Trp Leu Asn Gly Lys Glu Tyr Lys Cys Lys Val Ser Asn Lys Ala
            320                 325                 330

Leu Pro Ala Pro Ile Glu Lys Thr Ile Ser Lys Ala Lys Gly Gln
            335                 340                 345

Pro Arg Glu Pro Gln Val Tyr Thr Leu Pro Pro Ser Arg Glu Glu
            350                 355                 360

Met Thr Lys Asn Gln Val Ser Leu Thr Cys Leu Val Lys Gly Phe
            365                 370                 375

Tyr Pro Ser Asp Ile Ala Val Glu Trp Glu Ser Asn Gly Gln Pro
            380                 385                 390

Glu Asn Asn Tyr Lys Thr Thr Pro Pro Val Leu Asp Ser Asp Gly
            395                 400                 405

Ser Phe Phe Leu Tyr Ser Lys Leu Thr Val Asp Lys Ser Arg Trp
            410                 415                 420

Gln Gln Gly Asn Val Phe Ser Cys Ser Val Met His Glu Ala Leu
            425                 430                 435

His Asn His Tyr Thr Gln Lys Ser Leu Ser Leu Ser Pro Gly
            440                 445

<210> SEQ ID NO 3
<211> LENGTH: 214
<212> TYPE: PRT
<213> ORGANISM: Artificial sequence
<220> FEATURE:
<223> OTHER INFORMATION: Sequence is synthesized

<400> SEQUENCE: 3

Asp Ile Gln Met Thr Gln Ser Pro Ser Ser Leu Ser Ala Ser Val
 1               5                  10                  15

Gly Asp Arg Val Thr Ile Thr Cys Arg Ala Ser Lys Thr Ile Ser
                20                  25                  30

Lys Tyr Leu Ala Trp Tyr Gln Gln Lys Pro Gly Lys Ala Pro Lys
            35                  40                  45

Leu Leu Ile Tyr Ser Gly Ser Thr Leu Gln Ser Gly Val Pro Ser
         50                  55                  60

Arg Phe Ser Gly Ser Gly Ser Gly Thr Asp Phe Thr Leu Thr Ile
 65                  70                  75

Ser Ser Leu Gln Pro Glu Asp Phe Ala Thr Tyr Tyr Cys Gln Gln
             80                  85                  90

His Asn Glu Tyr Pro Leu Thr Phe Gly Gln Gly Thr Lys Val Glu
             95                 100                 105

Ile Lys Arg Thr Val Ala Ala Pro Ser Val Phe Ile Phe Pro Pro
            110                 115                 120

Ser Asp Glu Gln Leu Lys Ser Gly Thr Ala Ser Val Val Cys Leu
            125                 130                 135

Leu Asn Asn Phe Tyr Pro Arg Glu Ala Lys Val Gln Trp Lys Val
            140                 145                 150

Asp Asn Ala Leu Gln Ser Gly Asn Ser Gln Glu Ser Val Thr Glu
            155                 160                 165

Gln Asp Ser Lys Asp Ser Thr Tyr Ser Leu Ser Ser Thr Leu Thr
            170                 175                 180

Leu Ser Lys Ala Asp Tyr Glu Lys His Lys Val Tyr Ala Cys Glu
            185                 190                 195

Val Thr His Gln Gly Leu Ser Ser Pro Val Thr Lys Ser Phe Asn
            200                 205                 210

Arg Gly Glu Cys

<210> SEQ ID NO 4
<211> LENGTH: 451
<212> TYPE: PRT
<213> ORGANISM: Artificial sequence
<220> FEATURE:
<223> OTHER INFORMATION: Sequence is synthesized

<400> SEQUENCE: 4

```
Glu Val Gln Leu Val Glu Ser Gly Gly Leu Val Gln Pro Gly
 1               5                  10                  15

Gly Ser Leu Arg Leu Ser Cys Ala Ala Ser Gly Tyr Ser Phe Thr
                20                  25                  30

Gly His Trp Met Asn Trp Val Arg Gln Ala Pro Gly Lys Gly Leu
            35                  40                  45

Glu Trp Val Gly Met Ile His Pro Ser Asp Ser Glu Thr Arg Tyr
        50                  55                  60

Asn Gln Lys Phe Lys Asp Arg Phe Thr Ile Ser Val Asp Lys Ser
65                  70                  75

Lys Asn Thr Leu Tyr Leu Gln Met Asn Ser Leu Arg Ala Glu Asp
                80                  85                  90

Thr Ala Val Tyr Tyr Cys Ala Arg Gly Ile Tyr Phe Tyr Gly Thr
                95                 100                 105

Thr Tyr Phe Asp Tyr Trp Gly Gln Gly Thr Leu Val Thr Val Ser
                110                 115                 120

Ser Ala Ser Thr Lys Gly Pro Ser Val Phe Pro Leu Ala Pro Ser
                125                 130                 135

Ser Lys Ser Thr Ser Gly Gly Thr Ala Ala Leu Gly Cys Leu Val
                140                 145                 150

Lys Asp Tyr Phe Pro Glu Pro Val Thr Val Ser Trp Asn Ser Gly
                155                 160                 165

Ala Leu Thr Ser Gly Val His Thr Phe Pro Ala Val Leu Gln Ser
                170                 175                 180

Ser Gly Leu Tyr Ser Leu Ser Ser Val Val Thr Val Pro Ser Ser
                185                 190                 195

Ser Leu Gly Thr Gln Thr Tyr Ile Cys Asn Val Asn His Lys Pro
                200                 205                 210

Ser Asn Thr Lys Val Asp Lys Lys Val Glu Pro Lys Ser Cys Asp
                215                 220                 225

Lys Thr His Thr Cys Pro Pro Cys Pro Ala Pro Glu Leu Leu Gly
                230                 235                 240

Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly
                275                 280                 285

Val Glu Val His Asn Ala Lys Thr Lys Pro Arg Glu Glu Gln Tyr
                290                 295                 300

Asn Ser Thr Tyr Arg Val Val Ser Val Leu Thr Val Leu His Gln
                305                 310                 315

Asp Trp Leu Asn Gly Lys Glu Tyr Lys Cys Lys Val Ser Asn Lys
                320                 325                 330
```

```
Ala Leu Pro Ala Pro Ile Glu Lys Thr Ile Ser Lys Ala Lys Gly
                335                 340             345

Gln Pro Arg Glu Pro Gln Val Tyr Thr Leu Pro Pro Ser Arg Glu
                350                 355             360

Glu Met Thr Lys Asn Gln Val Ser Leu Thr Cys Leu Val Lys Gly
                365                 370             375

Phe Tyr Pro Ser Asp Ile Ala Val Glu Trp Glu Ser Asn Gly Gln
                380                 385             390

Pro Glu Asn Asn Tyr Lys Thr Thr Pro Pro Val Leu Asp Ser Asp
                395                 400             405

Gly Ser Phe Phe Leu Tyr Ser Lys Leu Thr Val Asp Lys Ser Arg
                410                 415             420

Trp Gln Gln Gly Asn Val Phe Ser Cys Ser Val Met His Glu Ala
                425                 430             435

Leu His Asn His Tyr Thr Gln Lys Ser Leu Ser Leu Ser Pro Gly
                440                 445             450

Lys
```